(12) United States Patent
Al Mahmood et al.

(10) Patent No.: US 8,742,067 B2
(45) Date of Patent: *Jun. 3, 2014

(54) ANTI-TUMOR DRUG, MEDICAMENT, COMPOSITION, AND USE THEREOF

(75) Inventors: Salman Al Mahmood, Paris (FR); Sylvie Colin, Paris (FR)

(73) Assignee: Gene Signal International SA, Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/600,329

(22) PCT Filed: May 16, 2008

(86) PCT No.: PCT/EP2008/056075
§ 371 (c)(1),
(2), (4) Date: Nov. 16, 2009

(87) PCT Pub. No.: WO2008/138994
PCT Pub. Date: Nov. 20, 2008

(65) Prior Publication Data
US 2010/0151051 A1    Jun. 17, 2010

(30) Foreign Application Priority Data
May 16, 2007  (EP) .................................... 07108349

(51) Int. Cl.
*C07K 5/00*    (2006.01)
*A61K 38/43*   (2006.01)

(52) U.S. Cl.
USPC ...... 530/300; 530/350; 424/277.1; 424/187.1

(58) Field of Classification Search
None
See application file for complete search history.

(56) References Cited

U.S. PATENT DOCUMENTS

| | | | |
|---|---|---|---|
| 6,743,619 B1 | 6/2004 | Tang et al. | |
| 6,919,193 B2 * | 7/2005 | Tang et al. | 435/195 |
| 2003/0219745 A1 | 11/2003 | Tang et al. | |
| 2004/0009491 A1 * | 1/2004 | Birse et al. | 435/6 |
| 2005/0106644 A1 | 5/2005 | Cairns et al. | |
| 2005/0119215 A1 * | 6/2005 | Al-Mahmood et al. | 514/44 |
| 2006/0079453 A1 * | 4/2006 | Sidney et al. | 514/12 |

FOREIGN PATENT DOCUMENTS

| | | | |
|---|---|---|---|
| WO | WO0190304 | * | 11/2001 |
| WO | 02081731 | | 10/2002 |
| WO | 02099116 | | 12/2002 |
| WO | 03080105 | | 10/2003 |

OTHER PUBLICATIONS

International Search Report dated Sep. 17, 2008, in PCT application.
Database EMBL [Online], Jun. 23, 2006, Bainbridge M N et al.: "Analysis of the prostate cancer cell line LNCaP transcriptome using a sequencing-by-synthesis approach" XP002496331 Database accession No. EC484852.

\* cited by examiner

*Primary Examiner* — Lei Yao
(74) *Attorney, Agent, or Firm* — Young & Thompson

(57) ABSTRACT

An active polypeptide comprising the amino acid sequence of SEQ ID NO:4, having an anti-tumor activity, and compositions and methods including the active polypeptide.

9 Claims, 7 Drawing Sheets

SEQUENCE LISTING

<160> NUMBER OF SEQ ID NOS: 23

<210> SEQ ID NO 1
<211> LENGTH: 6160
<212> TYPE: DNA
<213> ORGANISM: Homo sapiens

<400> SEQUENCE: 1

```
ctcgcgagga gagcggagca ggcgcgcggc ccaggcggag gagcgccgac tctggagcag      60
ccggagctgg aagaggagga ggaggagagg cggcggggaa ggaggaggag ggggagagtc     120
gctcccgccg ggcgagcatg gggcgcctgg cctcgaggcc gctgctgctg gcgctcctgt     180
cgttggctct ttgccgaggg cgtgtggtga gagtccccac agcgaccctg gttcgagtgg     240
tgggcactga gctggtcatc ccctgcaacg tcagtgacta tgatggcccc agcgagcaaa     300
actttgactg gagcttctca tctttgggga gcagctttgt ggagcttgca agcacctggg     360
aggtggggtt cccagcccag ctgtaccagg agcggctgca gaggggcgag atcctgttaa     420
ggcggactgc caacgacgcc gtggagctcc acataaagaa cgtccagcct tcagaccaag     480
gccactacaa atgttcaacc cccagcacag atgccactgt ccagggaaac tatgaggaca     540
cagtgcaggt taaagtgctg gccgactccc tgcacgtggg cccagcgcg cggccccgc      600 cgagcctgag cctgcgggag ggggagccct tcgagctgcg ctgcactgcc gcctccgcct     660
```

```
cgccgctgca cacgcacctg gcgctgctgt gggaggtgca ccgcggcccg gccaggcgga    720
gcgtcctcgc cctgacccac gagggcaggt tccacccggg cctggggtac gagcagcgct    780
accacagtgg ggacgtgcgc ctcgacaccg tgggcagcga cgcctaccgc ctctcagtgt    840
cccgggctct gtctgccgac cagggctcct acaggtgtat cgtcagcgag tggatcgccg    900
agcagggcaa ctggcaggaa atccaagaaa aggccgtgga agttgccacc gtggtgatcc    960
agccatcagt tctgcgagca gctgtgccca agaatgtgtc tgtggctgaa ggaaaggaac   1020
tggacctgac ctgtaacatc acaacagacc gagccgatga cgtccggccc gaggtgacgt   1080
ggtccttcag caggatgcct gacagcaccc tacctggctc ccgcgtgttg gcgcggcttg   1140
accgtgattc cctggtgcac agctcgcctc atgttgcttt gagtcatgtg gatgcacgct   1200
cctaccattt actggttcgg gatgttagca agaaaactc tggctactat tactgccacg   1260
tgtccctgtg ggcacccgga cacaacagga gctggcacaa agtggcagag gccgtgtctt   1320
ccccagctgg tgtgggtgtg acctggctag aaccagacta ccaggtgtac ctgaatgctt   1380
ccaaggtccc cggtttgcg gatgaccca cagagctggc atgccgggtg gtggacacga   1440
agagtgggga ggcgaatgtc cgattcacgg tttcgtggta ctacaggatg aaccggcgca   1500
gcgacaatgt ggtgaccagc gagctgcttg cagtcatgga cggggactgg acgctaaaat   1560
atggagagag gagcaagcag cgggcccagg atggagactt tatttttttct aaggaacata   1620
cagacacgtt caatttccgg atccaaagga ctacagagga agacagaggc aattattact   1680
gtgttgtgtc tgcctggacc aaacagcgga caacagctg ggtgaaaagc aaggatgtct   1740
tctccaagcc tgttaacata ttttgggcat agaagattc cgtgcttgtg gtgaaggcga   1800
ggcagccaaa gcctttcttt gctgccgaa atacatttga gatgacttgc aaagtatctt   1860
ccaagaatat taagtcgcca cgctactctg ttctcatcat ggctgagaag cctgtcggcg   1920
acctctccag tcccaatgaa acgaagtaca tcatctctct ggaccaggat tctgtggtga   1980
agctggagaa ttggacagat gcatcacggg tggatggcgt tgttttagaa aaagtgcagg   2040
aggatgagtt ccgctatcga atgtaccaga ctcaggtctc agacgcaggg ctgtaccgct   2100
gcatggtgac agcctggtct cctgtcaggg gcagcctttg gcgagaagca gcaaccagtc   2160
tctccaatcc tattgagata gacttccaaa cctcaggtcc tatatttaat gcttctgtgc   2220
attcagacac accatcagta attcggggag atctgatcaa attgttctgt atcatcactg   2280
tcgagggagc agcactggat ccagatgaca tggccttga tgtgtcctgg tttgcggtgc   2340
actcttttgg cctggacaag gctcctgtgc tcctgtcttc cctggatcgg aagggcatcg   2400
tgaccacctc ccggagggac tggaagagcg acctcagcct ggagcgcgtg agtgtgctgg   2460
aattcttgct gcaagtgcat ggctccgagg accaggactt tggcaactac tactgttccg   2520
tgactccatg ggtgaagtca ccaacaggtt cctggcagaa ggaggcagag atccactcca   2580
agcccgtttt tataactgtg aagatggatg tgctgaacgc cttcaagtat cccttgctga   2640
tcggcgtcgg tctgtccacg gtcatcgggc tcctgtcctg tctcatcggg tactgcagct   2700
cccactggtt ttgtaagaag gaggttcagg agacacggcg cgagcgccgc aggctcatgt   2760
cgatggagat ggactaggct ggcccgggag gggagtgaca gagggacgtt ctaggagcaa   2820
ttggggcaag aagaggacag tgatatttta aaacaaagtg tgttacacta aaaaccagtc   2880
ctctctaatc tcaggtggga cttggcgctc tctcttttct gcatgtcaag ttctgagcgc   2940
ggacatgttt accagcacac ggctcttctt cccacggcac tttctgatgt aacaatcgag   3000
tgtgtgtttt cccaactgca gctttttaat ggttaacctt catctaattt ttttctccc   3060
```

-continued

```
actggtttat agatcctctg acttgtgtgt gtttatagct tttgtttcgc ggggttgtgg    3120
tgaggaaggg gtgatggcat gcggagttct ttatcttcag tgagaatgtg cctgcccgcc    3180
tgagagccag cttccgcgtt ggaggcacgt gttcagagag ctgctgagcg ccaccctcta    3240
cccggctgac agacaacaca gacctgtgcc gaaggctaat ttgtggcttt tacgacccta    3300
ccccaccccc tgttttcagg ggtttagact acatttgaaa tccaaacttg gagtatataa    3360
cttcttattg agcccaactg cttttttttt tttttttttt gcttctctgc ccttttcca    3420
tttcttttgt atttgttttc tgtgagagca ctgaaatggc agccctggaa tctacaattt    3480
ggctctccac tgagcacctt atcttgccac cttagcctta agaatgaata tgaagaaaaa    3540
tacacagcca cctctgtcca gggcagtaag aagggctgca aggaagggga ggatggggac    3600
aaggaaagga tcagatacct gctccagtag ttgtgaggcc actgtgtctc agggggactcc   3660
aggaggagca gaagagggat cccacgaagt tattcttacg cagctggggc caggagggtc    3720
agagtggtgc caggtgcaag ttaggctaaa gaagccacca ctattcctct ctcttgccca    3780
ttgtgggggg caaaggcatt ggtcaccaag agtcttgcag ggggacccac agatatgcca    3840
tgtccttcac acgtgcttgg gctccttaac ctgaaggcaa attgctactt gcaagactga    3900
ctgacttcaa ggaatcagaa attacctaga agcaccatgt ttttctatg acctttttcag   3960
tccttcaggt cattttaagg tccactgcag ggggttagtg agaaagggta tactttgtgg    4020
tatgttttgc tttcctaata gggacatgaa ggaaacccag caatttgctg ttatgtgaat    4080
ggcctgtaga gcagagtcaa gagcggtgtg ctttgcccga ctgctcccat caggaatagg    4140
agagtagaca gagatcttcc acatcccagg cttctgctgc tgctttaaaa gctctgtcct    4200
tggagcctcc cgctccctga agtgtctcgc cccctgcaca gcactggcct ttcggaagca    4260
tcccagtagg gttttctgag gctcgctggt gactcatgcc ctaattgcaa tcctctgctt    4320
ttatcttgac tttgaaggat ctaacactgc tctctcttcc aaagggaaa aaaagattca    4380
tttgtttga gcaataaact aatacaaat gatggccatt catgtgcagc tctttgtcac    4440
catgggccgg atgagttgtg ctcctcctgg ctcaccattt cccctgctc ccccacagcc    4500
ggttctgcac ttatcaccga gtcgcccctg gaagcagatt cccattgagt tttccccacc    4560
aaggggacca tgcacatggt agaaacatta gattctgcat tgacagtagc ctttccttgg    4620
cccgggcctg tggtgggaag acgggcaaca agtatacccc accagggcct gagtgactag    4680
aggaagagga cgaggccttg ttggcactag atttgggtat tttctgcatg tcataacata    4740
tcctaactgc tatttcagaa gaggcagctt gtaggtgatt gtacaagtga gaattaaaga    4800
gagaacagat atttaaacag gtgctgtatt agtaacagcc agtgcccttt cagcccttgc    4860
atctattaaa aggagattca ggattttatt ggcacaggcc cttcttagta ggaagaaagg    4920
gtgcttagct ttggacctga ccgggtgtgt gtaaaccat ggactgagtc acagcagaca    4980
ctcgatggtg gtaaatgtga tgggtgctta cacactgtac cttttccttt catactgatg    5040
ctgcagttca gggctggagt tgttaaggca ttgacctcca cccacctgcc ccatgtccac    5100
tgggctgccc aagctgcatg tcacctgagg gctggcagga aggggcgaga aatcccaggg    5160
cattgtacca aggacctagt tccttctagg gatataaatt tccaggaatg tgtattttta    5220
atgtggtgag atgcactctt ttgttgtacc aaatagggct ccccaccccca ccctgcgac    5280
aagtgctctt ctagaacagg ttcctaccag cagcactggt gtgaatgaaa gagagaccca    5340
gccgcgtctc acacaggtgg aattgcactt cttaacaaaa aggaacttta taaaagtttg    5400
ggattttttt tcctaatcat aaaaatagcc ccagaaagag cctaagctat gttcagatag    5460
```

```
aagcctcgaa attcctgtaa attgtttact ttatgatgtt tacatacacg tttcactttg    5520
aaaaaaaatg caaatcgact ttttaacaac tgttgagatg tttcatggga cagtagaact    5580
ctgactcacc aactgggcta aattttaatt taaaaatgta tttatttgag tgtctttccc    5640
cccctcaccc tcaccatctg aggggctccc tgagatcttg gtagaggagg ccctcctgc     5700 ccagaccttc gtttgtttcc ccggtggccc ttgcttcttg ctttgcagac tgcctgcagc    5760
catgattttg tcactgacat ctgtgagcca aagactgagc ttttttggca ggaataataa    5820
gcaatactac acaacttgct actttcagaa aactttttt tagcttcacc gatgacaaca     5880
gaggaagaag ggaactggga tttgggtaag ttctcctcca ctgtttgacc aaattctcag    5940
tgataaatat gtgtgcagat ccctagaaga gaaaacgctg actttctttt taagtgtggc    6000
acataaggat ctgcagaatt ttccgtagac aaagaaagga tcttgtgtat ttttgtccat    6060
atccaatgtt atatgaacta attgtattgt tttatactgt gaccacaaat attatgcaat    6120
gcaccatttg ttttttattt cattaaagga agtttaattt                          6160
```

<210> SEQ ID NO 2
<211> LENGTH: 924
<212> TYPE: PRT
<213> ORGANISM: Homo sapiens

<400> SEQUENCE: 2

```
Arg Glu Glu Ser Gly Ala Gly Ala Arg Pro Arg Arg Ser Ala Asp
1               5                   10                  15

Ser Gly Ala Ala Gly Ala Gly Arg Gly Gly Gly Glu Ala Ala Gly
                20                  25                  30

Lys Glu Glu Gly Glu Ser Arg Ser Arg Arg Ala Ser Met Gly Arg
                35                  40                  45

Leu Ala Ser Arg Pro Leu Leu Leu Ala Leu Leu Ser Leu Ala Leu Cys
        50                  55                  60

Arg Gly Arg Val Val Arg Val Pro Thr Ala Thr Leu Val Arg Val Val
65                  70                  75                  80

Gly Thr Glu Leu Val Ile Pro Cys Asn Val Ser Asp Tyr Asp Gly Pro
                85                  90                  95

Ser Glu Gln Asn Phe Asp Trp Ser Phe Ser Ser Leu Gly Ser Ser Phe
                100                 105                 110

Val Glu Leu Ala Ser Thr Trp Glu Val Gly Phe Pro Ala Gln Leu Tyr
            115                 120                 125

Gln Glu Arg Leu Gln Arg Gly Glu Ile Leu Leu Arg Arg Thr Ala Asn
        130                 135                 140

Asp Ala Val Glu Leu His Ile Lys Asn Val Gln Pro Ser Asp Gln Gly
145                 150                 155                 160

His Tyr Lys Cys Ser Thr Pro Ser Thr Asp Ala Thr Val Gln Gly Asn
                165                 170                 175

Tyr Glu Asp Thr Val Gln Val Lys Val Leu Ala Asp Ser Leu His Val
            180                 185                 190

Gly Pro Ser Ala Arg Pro Pro Ser Leu Ser Leu Arg Glu Gly Glu
        195                 200                 205

Pro Phe Glu Leu Arg Cys Thr Ala Ala Ser Ala Ser Pro Leu His Thr
    210                 215                 220

His Leu Ala Leu Leu Trp Glu Val His Arg Gly Pro Ala Arg Arg Ser
225                 230                 235                 240

Val Leu Ala Leu Thr His Glu Gly Arg Phe His Pro Gly Leu Gly Tyr
                245                 250                 255
```

-continued

```
Glu Gln Arg Tyr His Ser Gly Asp Val Arg Leu Asp Thr Val Gly Ser
                260                 265                 270

Asp Ala Tyr Arg Leu Ser Val Ser Arg Ala Leu Ser Ala Asp Gln Gly
            275                 280                 285

Ser Tyr Arg Cys Ile Val Ser Glu Trp Ile Ala Glu Gln Gly Asn Trp
        290                 295                 300

Gln Glu Ile Gln Glu Lys Ala Val Glu Val Ala Thr Val Val Ile Gln
305                 310                 315                 320

Pro Ser Val Leu Arg Ala Val Pro Lys Asn Val Ser Val Ala Glu
                325                 330                 335

Gly Lys Glu Leu Asp Leu Thr Cys Asn Ile Thr Thr Arg Ala Asp
                340                 345                 350

Asp Val Arg Pro Glu Val Thr Trp Ser Phe Ser Arg Met Pro Asp Ser
            355                 360                 365

Thr Leu Pro Gly Ser Arg Val Leu Ala Arg Leu Asp Arg Asp Ser Leu
        370                 375                 380

Val His Ser Ser Pro His Val Ala Leu Ser His Val Asp Ala Arg Ser
385                 390                 395                 400

Tyr His Leu Leu Val Arg Asp Val Ser Lys Glu Asn Ser Gly Tyr Tyr
                405                 410                 415

Tyr Cys His Val Ser Leu Trp Ala Pro Gly His Asn Arg Ser Trp His
            420                 425                 430

Lys Val Ala Glu Ala Val Ser Ser Pro Ala Gly Val Gly Val Thr Trp
        435                 440                 445

Leu Glu Pro Asp Tyr Gln Val Tyr Leu Asn Ala Ser Lys Val Pro Gly
    450                 455                 460

Phe Ala Asp Asp Pro Thr Glu Leu Ala Cys Arg Val Val Asp Thr Lys
465                 470                 475                 480

Ser Gly Glu Ala Asn Val Arg Phe Thr Val Ser Trp Tyr Tyr Arg Met
                485                 490                 495

Asn Arg Arg Ser Asp Asn Val Val Thr Ser Glu Leu Leu Ala Val Met
            500                 505                 510

Asp Gly Asp Trp Thr Leu Lys Tyr Gly Glu Arg Ser Lys Gln Arg Ala
        515                 520                 525

Gln Asp Gly Asp Phe Ile Phe Ser Lys Glu His Thr Asp Thr Phe Asn
    530                 535                 540

Phe Arg Ile Gln Arg Thr Thr Glu Glu Asp Arg Gly Asn Tyr Tyr Cys
545                 550                 555                 560

Val Val Ser Ala Trp Thr Lys Gln Arg Asn Asn Ser Trp Val Lys Ser
                565                 570                 575

Lys Asp Val Phe Ser Lys Pro Val Asn Ile Phe Trp Ala Leu Glu Asp
            580                 585                 590

Ser Val Leu Val Val Lys Ala Arg Gln Pro Lys Pro Phe Phe Ala Ala
        595                 600                 605

Gly Asn Thr Phe Glu Met Thr Cys Lys Val Ser Ser Lys Asn Ile Lys
    610                 615                 620

Ser Pro Arg Tyr Ser Val Leu Ile Met Ala Glu Lys Pro Val Gly Asp
625                 630                 635                 640

Leu Ser Ser Pro Asn Glu Thr Lys Tyr Ile Ile Ser Leu Asp Gln Asp
                645                 650                 655

Ser Val Val Lys Leu Glu Asn Trp Thr Asp Ala Ser Arg Val Asp Gly
            660                 665                 670

Val Val Leu Glu Lys Val Gln Glu Asp Glu Phe Arg Tyr Arg Met Tyr
        675                 680                 685
```

Gln Thr Gln Val Ser Asp Ala Gly Leu Tyr Arg Cys Met Val Thr Ala
    690                 695                 700

Trp Ser Pro Val Arg Gly Ser Leu Trp Arg Glu Ala Ala Thr Ser Leu
705                 710                 715                 720

Ser Asn Pro Ile Glu Ile Asp Phe Gln Thr Ser Gly Pro Ile Phe Asn
                725                 730                 735

Ala Ser Val His Ser Asp Thr Pro Ser Val Ile Arg Gly Asp Leu Ile
            740                 745                 750

Lys Leu Phe Cys Ile Ile Thr Val Glu Gly Ala Ala Leu Asp Pro Asp
        755                 760                 765

Asp Met Ala Phe Asp Val Ser Trp Phe Ala Val His Ser Phe Gly Leu
    770                 775                 780

Asp Lys Ala Pro Val Leu Leu Ser Ser Leu Asp Arg Lys Gly Ile Val
785                 790                 795                 800

Thr Thr Ser Arg Arg Asp Trp Lys Ser Asp Leu Ser Leu Glu Arg Val
                805                 810                 815

Ser Val Leu Glu Phe Leu Leu Gln Val His Gly Ser Glu Asp Gln Asp
            820                 825                 830

Phe Gly Asn Tyr Tyr Cys Ser Val Thr Pro Trp Val Lys Ser Pro Thr
        835                 840                 845

Gly Ser Trp Gln Lys Glu Ala Glu Ile His Ser Lys Pro Val Phe Ile
    850                 855                 860

Thr Val Lys Met Asp Val Leu Asn Ala Phe Lys Tyr Pro Leu Leu Ile
865                 870                 875                 880

Gly Val Gly Leu Ser Thr Val Ile Gly Leu Leu Ser Cys Leu Ile Gly
                885                 890                 895

Tyr Cys Ser Ser His Trp Cys Cys Lys Lys Glu Val Gln Glu Thr Arg
            900                 905                 910

Arg Glu Arg Arg Arg Leu Met Ser Met Glu Met Asp
        915                 920

<210> SEQ ID NO 3
<211> LENGTH: 327
<212> TYPE: DNA
<213> ORGANISM: Homo sapiens

<400> SEQUENCE: 3
atggcctttg atgtgtcctg gtttgcggtg cactcttttg gcctggacaa ggctcctgtg      60
ctcctgtctt ccctggatcg gaagggcatc gtgaccacct cccggaggga ctggaagagc     120
gacctcagcc tggagcgcgt gagtgtgctg gaattcttgc tgcaagtgca tggctccgag     180
gaccaggact ttggcaacta ctactgttcc gtgactccat gggtgaagtc accaacaggt     240
tcctggcaga aggaggcaga gatccactcc aagcccgttt ttataactgt gaagatggat     300
gtgctgaacg ccttcaagta tccctga                                         327

<210> SEQ ID NO 4
<211> LENGTH: 108
<212> TYPE: PRT
<213> ORGANISM: Homo sapiens

<400> SEQUENCE: 4

Met Ala Phe Asp Val Ser Trp Phe Ala Val His Ser Phe Gly Leu Asp
1               5                   10                  15

Lys Ala Pro Val Leu Leu Ser Ser Leu Asp Arg Lys Gly Ile Val Thr
            20                  25                  30

```
Thr Ser Arg Arg Asp Trp Lys Ser Asp Leu Ser Leu Glu Arg Val Ser
         35                  40                  45

Val Leu Glu Phe Leu Leu Gln Val His Gly Ser Glu Asp Gln Asp Phe
 50                  55                  60

Gly Asn Tyr Tyr Cys Ser Val Thr Pro Trp Val Lys Ser Pro Thr Gly
 65                  70                  75                  80

Ser Trp Gln Lys Glu Ala Glu Ile His Ser Lys Pro Val Phe Ile Thr
                 85                  90                  95

Val Lys Met Asp Val Leu Asn Ala Phe Lys Tyr Pro
                100                 105

<210> SEQ ID NO 5
<211> LENGTH: 1049
<212> TYPE: DNA
<213> ORGANISM: Homo sapiens
<220> FEATURE:
<221> NAME/KEY: misc_feature
<222> LOCATION: (960)..(960)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (977)..(978)
<223> OTHER INFORMATION: n is a, c, g, or t
<220> FEATURE:
<221> NAME/KEY: misc_feature
<222> LOCATION: (981)..(981)
<223> OTHER INFORMATION: n is a, c, g, or t
<220> FEATURE:
<221> NAME/KEY: misc_feature
<222> LOCATION: (994)..(996)
<223> OTHER INFORMATION: n is a, c, g, or t
<220> FEATURE:
<221> NAME/KEY: misc_feature
<222> LOCATION: (998)..(998)
<223> OTHER INFORMATION: n is a, c, g, or t
<220> FEATURE:
<221> NAME/KEY: misc_feature
<222> LOCATION: (1012)..(1013)
<223> OTHER INFORMATION: n is a, c, g, or t
<220> FEATURE:
<221> NAME/KEY: misc_feature
<222> LOCATION: (1019)..(1019)
<223> OTHER INFORMATION: n is a, c, g, or t
<220> FEATURE:
<221> NAME/KEY: misc_feature
<222> LOCATION: (1023)..(1023)
<223> OTHER INFORMATION: n is a, c, g, or t
<220> FEATURE:
<221> NAME/KEY: misc_feature
<222> LOCATION: (1029)..(1029)
<223> OTHER INFORMATION: n is a, c, g, or t
<220> FEATURE:
<221> NAME/KEY: misc_feature
<222> LOCATION: (1036)..(1036)
<223> OTHER INFORMATION: n is a, c, g, or t
<220> FEATURE:
<221> NAME/KEY: misc_feature
<222> LOCATION: (1047)..(1047)
<223> OTHER INFORMATION: n is a, c, g, or t

<400> SEQUENCE: 5
ttcccctcta gaataaattt tgtttaactt taagaaggag atatacatat gcaccatcat      60
catcatcatt cttctggtct ggtgccacgc ggttctggta tgaaagaaac cgctgctgct     120
aaattcgaac gccagcacat ggacagccca gatctgggta ccgatgacga cgacaagatg     180 gccttttgatg tgtcctggtt tgcggtgcac tcttttggcc tggacaaggc tcctgtgctc     240
ctgtcttccc tggatcggaa gggcatcgtg accaccctccc ggagggactg gaagagcgac     300
```

```
ctcagcctgg agcgcgtgag tgtgctggaa ttcttgctgc aagtgcatgg ctccgaggac    360
caggactttg gcaactacta ctgttccgtg actccatggg tgaagtcacc aacaggttcc    420
tggcagaagg aggcagagat ccactccaag cccgttttta taactgtgaa gatggatgtg    480
ctgaacgcct tcaagtatcc ctgaaccggg cttctcctca accatggcga tatcggatcc    540
gaattcgagc tccgtcgaca gcttgcggc cgcactcgag caccaccacc accaccactg     600
agatccggct gctaacaaag cccgaaagga agctgagttg gctgctgcca ccgctgagca    660
ataactagca taacccttg gggcctctaa acgggtcttg aggggttttt tgctgaaagg     720
aggaactata tccggattgg cgaatgggac gcgccctgta gcggcgcatt aagcgcggcg    780
ggtgtggtgg ttacgcgcag cgtgaccgct acacttgcca gcgccctagc gcccgctctt    840
tcgctttctt ccttcctttc tcgccacgtt cgccggcttt cccgtcaag ctctaaatcg     900
gggctccctt tagggttccg atttagtgct tacggccctc gaccccaaaa acttgattan    960
gggatggtt cacgtanngg ncatcccctg atanngngtt ttcgcctttg anntggagnc     1020
ccnttcttna tagggnacct tgttccnaa                                      1049
```

<210> SEQ ID NO 6
<211> LENGTH: 151
<212> TYPE: PRT
<213> ORGANISM: Homo sapiens

<400> SEQUENCE: 6

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Met Ala Phe Asp Val
        35                  40                  45

Ser Trp Phe Ala Val His Ser Phe Gly Leu Asp Lys Ala Pro Val Leu
    50                  55                  60

Leu Ser Ser Leu Asp Arg Lys Gly Ile Val Thr Thr Ser Arg Arg Asp
65                  70                  75                  80

Trp Lys Ser Asp Leu Ser Leu Glu Arg Val Ser Val Leu Glu Phe Leu
                85                  90                  95

Leu Gln Val His Gly Ser Glu Asp Gln Asp Phe Gly Asn Tyr Tyr Cys
            100                 105                 110

Ser Val Thr Pro Trp Val Lys Ser Pro Thr Gly Ser Trp Gln Lys Glu
        115                 120                 125

Ala Glu Ile His Ser Lys Pro Val Phe Ile Thr Val Lys Met Asp Val
    130                 135                 140

Leu Asn Ala Phe Lys Tyr Pro
145                 150

<210> SEQ ID NO 7
<211> LENGTH: 90
<212> TYPE: PRT
<213> ORGANISM: Homo sapiens

<400> SEQUENCE: 7

Met Ala Phe Asp Val Ser Trp Phe Ala Val His Ser Phe Gly Leu Asp
1               5                   10                  15

Lys Ala Pro Val Leu Leu Ser Ser Leu Asp Arg Lys Gly Ile Val Thr
            20                  25                  30

Thr Ser Arg Arg Asp Trp Lys Ser Asp Leu Ser Leu Glu Arg Val Ser

```
                35                  40                  45
Val Leu Glu Phe Leu Leu Gln Val His Gly Ser Glu Asp Gln Asp Phe
 50                  55                  60
Gly Asn Tyr Tyr Cys Ser Val Thr Pro Trp Val Lys Ser Pro Thr Gly
 65                  70                  75                  80
Ser Trp Gln Lys Glu Ala Glu Ile His Ser
                 85                  90

<210> SEQ ID NO 8
<211> LENGTH: 77
<212> TYPE: PRT
<213> ORGANISM: Homo sapiens

<400> SEQUENCE: 8

Met Ala Phe Asp Val Ser Trp Phe Ala Val His Ser Phe Gly Leu Asp
  1               5                  10                  15
Lys Ala Pro Val Leu Leu Ser Ser Leu Asp Arg Lys Gly Ile Val Thr
                 20                  25                  30
Thr Ser Arg Arg Asp Trp Lys Ser Asp Leu Ser Leu Glu Arg Val Ser
                 35                  40                  45
Val Leu Glu Phe Leu Leu Gln Val His Gly Ser Glu Asp Gln Asp Phe
 50                  55                  60
Gly Asn Tyr Tyr Cys Ser Val Thr Pro Trp Val Lys Ser
 65                  70                  75

<210> SEQ ID NO 9
<211> LENGTH: 66
<212> TYPE: PRT
<213> ORGANISM: Homo sapiens

<400> SEQUENCE: 9

Met Ala Phe Asp Val Ser Trp Phe Ala Val His Ser Phe Gly Leu Asp
  1               5                  10                  15
Lys Ala Pro Val Leu Leu Ser Ser Leu Asp Arg Lys Gly Ile Val Thr
                 20                  25                  30
Thr Ser Arg Arg Asp Trp Lys Ser Asp Leu Ser Leu Glu Arg Val Ser
                 35                  40                  45
Val Leu Glu Phe Leu Leu Gln Val His Gly Ser Glu Asp Gln Asp Phe
 50                  55                  60
Gly Asn
 65

<210> SEQ ID NO 10
<211> LENGTH: 51
<212> TYPE: PRT
<213> ORGANISM: Homo sapiens

<400> SEQUENCE: 10

Met Ala Phe Asp Val Ser Trp Phe Ala Val His Ser Phe Gly Leu Asp
  1               5                  10                  15
Lys Ala Pro Val Leu Leu Ser Ser Leu Asp Arg Lys Gly Ile Val Thr
                 20                  25                  30
Thr Ser Arg Arg Asp Trp Lys Ser Asp Leu Ser Leu Glu Arg Val Ser
                 35                  40                  45
Val Leu Glu
 50

<210> SEQ ID NO 11
<211> LENGTH: 37
```

<212> TYPE: PRT
<213> ORGANISM: Homo sapiens

<400> SEQUENCE: 11

Met Ala Phe Asp Val Ser Trp Phe Ala Val His Ser Phe Gly Leu Asp
1               5                   10                  15

Lys Ala Pro Val Leu Leu Ser Ser Leu Asp Arg Lys Gly Ile Val Thr
            20                  25                  30

Thr Ser Arg Arg Asp
        35

<210> SEQ ID NO 12
<211> LENGTH: 20
<212> TYPE: PRT
<213> ORGANISM: Homo sapiens

<400> SEQUENCE: 12

Met Ala Phe Asp Val Ser Trp Phe Ala Val His Ser Phe Gly Leu Asp
1               5                   10                  15

Lys Ala Pro Val
            20

<210> SEQ ID NO 13
<211> LENGTH: 270
<212> TYPE: DNA
<213> ORGANISM: Homo sapiens

<400> SEQUENCE: 13
atggcctttg atgtgtcctg gtttgcggtg cactcttttg gcctggacaa ggctcctgtg      60
ctcctgtctt ccctggatcg aagggcatc gtgaccacct cccggaggga ctggaagagc      120
gacctcagcc tggagcgcgt gagtgtgctg gaattcttgc tgcaagtgca tggctccgag    180
gaccaggact ttggcaacta ctactgttcc gtgactccat gggtgaagtc accaacaggt    240
tcctggcaga aggaggcaga gatccactcc                                       270

<210> SEQ ID NO 14
<211> LENGTH: 231
<212> TYPE: DNA
<213> ORGANISM: Homo sapiens

<400> SEQUENCE: 14
atggcctttg atgtgtcctg gtttgcggtg cactcttttg gcctggacaa ggctcctgtg      60
ctcctgtctt ccctggatcg aagggcatc gtgaccacct cccggaggga ctggaagagc      120
gacctcagcc tggagcgcgt gagtgtgctg gaattcttgc tgcaagtgca tggctccgag    180
gaccaggact ttggcaacta ctactgttcc gtgactccat gggtgaagtc a              231

<210> SEQ ID NO 15
<211> LENGTH: 198
<212> TYPE: DNA
<213> ORGANISM: Homo sapiens

<400> SEQUENCE: 15
atggcctttg atgtgtcctg gtttgcggtg cactcttttg gcctggacaa ggctcctgtg      60
ctcctgtctt ccctggatcg aagggcatc gtgaccacct cccggaggga ctggaagagc      120
gacctcagcc tggagcgcgt gagtgtgctg gaattcttgc tgcaagtgca tggctccgag    180
gaccaggact ttggcaac                                                    198

<210> SEQ ID NO 16

```
<211> LENGTH: 153
<212> TYPE: DNA
<213> ORGANISM: Homo sapiens

<400> SEQUENCE: 16
atggcctttg atgtgtcctg gtttgcggtg cactcttttg gcctggacaa ggctcctgtg      60
ctcctgtctt ccctggatcg aagggcatc gtgaccacct cccggaggga ctggaagagc     120
gacctcagcc tggagcgcgt gagtgtgctg gaa                                  153

<210> SEQ ID NO 17
<211> LENGTH: 111
<212> TYPE: DNA
<213> ORGANISM: Homo sapiens

<400> SEQUENCE: 17
atggcctttg atgtgtcctg gtttgcggtg cactcttttg gcctggacaa ggctcctgtg      60
ctcctgtctt ccctggatcg aagggcatc gtgaccacct cccggaggga c              111

<210> SEQ ID NO 18
<211> LENGTH: 60
<212> TYPE: DNA
<213> ORGANISM: Homo sapiens

<400> SEQUENCE: 18
atggcctttg atgtgtcctg gtttgcggtg cactcttttg gcctggacaa ggctcctgtg      60

<210> SEQ ID NO 19
<211> LENGTH: 37
<212> TYPE: DNA
<213> ORGANISM: Homo sapiens

<400> SEQUENCE: 19
gacgacgaca agatggcctt tgatgtgtcc tggtttg                               37

<210> SEQ ID NO 20
<211> LENGTH: 43
<212> TYPE: DNA
<213> ORGANISM: Homo sapiens

<400> SEQUENCE: 20
gaggagaagc ccggttcagg gatacttgaa ggcgttcagc aca                        43

<210> SEQ ID NO 21
<211> LENGTH: 6172
<212> TYPE: DNA
<213> ORGANISM: homo sapiens

<400> SEQUENCE: 21
ctcgcgagga gagcggagca ggcgcgcggc ccaggcggag gagcgccgac tctggagcag      60
ccggagctgg aagaggagga ggaggagagg cggcggggaa ggaggaggag ggggagagtc     120
gctcccgccg ggcgagcatg gggcgcctgg cctcgaggcc gctgctgctg gcgctcctgt     180
cgttggctct ttgccgaggg cgtgtggtga gagtccccac agcgaccctg gttcgagtgg     240
tgggcactga gctggtcatc ccctgcaacg tcagtgacta tgatggcccc agcgagcaaa     300
actttgactg gagcttctca tctttgggga gcagctttgt ggagcttgca agcacctggg     360
aggtggggtt cccagcccag ctgtaccagg agcggctgca gagggcgag atcctgttaa      420 ggcggactgc caacgacgcc gtggagctcc acataaagaa cgtccagcct tcagaccaag     480
gccactacaa atgttcaacc cccagcacag atgccactgt ccaggaaac tatgaggaca     540
```

```
cagtgcaggt taaagtgctg gccgactccc tgcacgtggg ccccagcgcg cggccccgc      600
cgagcctgag cctgcgggag ggggagccct tcgagctgcg ctgcactgcc gcctccgcct     660
cgccgctgca cacgcacctg cgctgctgt gggaggtgca ccgcggcccg gccaggcgga     720
gcgtcctcgc cctgacccac gagggcaggt tccacccggg cctggggtac gagcagcgct     780
accacagtgg ggacgtgcgc ctcgacaccg tgggcagcga cgcctaccgc ctctcagtgt     840
cccgggctct gtctgccgac cagggctcct acaggtgtat cgtcagcgag tggatcgccg     900
agcagggcaa ctggcaggaa atccaagaaa aggccgtgga agttgccacc gtggtgatcc     960
agccgacagt tctgcgagca gctgtgccca agaatgtgtc tgtggctgaa ggaaaggaac    1020
tggacctgac ctgtaacatc acaacagacc gagccgatga cgtccggccc gaggtgacgt    1080
ggtccttcag caggatgcct gacagcaccc tacctggctc ccgcgtgttg gcgcggcttg    1140
accgtgattc cctggtgcac agctcgcctc atgttgcttt gagtcatgtg gatgcacgct    1200
cctaccattt actggttcgg gatgttagca agaaaactc tggctactat tactgccacg     1260
tgtccctgtg ggcacccgga cacaacagga gctggcacaa agtggcagag gccgtgtctt    1320
ccccagctgg tgtgggtgtg acctggctag aaccagacta ccaggtgtac ctgaatgctt    1380
ccaaggtccc cgggtttgcg gatgaccca cagagctggc atgccaggtg gtggacacga     1440
agagtgggga ggcgaatgtc cgattcacgg tttcgtggta ctacaggatg aaccggcgca    1500
gcgacaatgt ggtgaccagc gagctgcttg cagtcatgga cggggactgg acgctaaaat    1560
atggagagag gagcaagcag cgggcccagg atggagactt tatttttct aaggaacata     1620
cagacacgtt caatttccgg atccaaagga ctacagagga agacagaggc aattattact    1680
gtgttgtgtc tgcctggacc aaacagcgga acaacagctg ggtgaaaagc aaggatgtct    1740
tctccaagcc tgttaacata ttttgggcat tagaagattc cgtgcttgtg gtgaaggcga    1800
ggcagccaaa gcctttcttt gctgccgaa atacatttga gatgacttgc aaagtatctt     1860
ccaagaatat taagtcgcca cgctactctg ttctcatcat ggctgagaag cctgtcggcg    1920
acctctccag tcccaatgaa acgaagtaca tcatctctct ggaccaggat tctgtggtga    1980
agctggagaa ttgacagat gcatcacggg tggatggcgt tgtttagaa aaagtgcagg      2040
aggatgagtt ccgctatcga atgtaccaga ctcaggtctc agacgcaggg ctgtaccgct    2100
gcatggtgac agcctggtct cctgtcaggg gcagcctttg gcgagaagca gcaaccagtc    2160
tctccaatcc tattgagata gacttccaaa cctcaggtcc tatatttaat gcttctgtgc    2220
attcagacac accatcagta attcggggag atctgatcaa attgttctgt atcatcactg    2280
tcgagggagc agcactggat ccagatgaca tggcctttga tgtgtcctgg tttgcggtgc    2340
actcttttgg cctggacaag gctcctgtgc tcctgtcttc cctggatcgg aagggcatcg    2400
tgaccaccctc ccggagggac tggaagagcg acctcagcct ggagcgcgtg agtgtgctgg   2460
aattcttgct gcaagtgcat ggctccgagg accaggactt tggcaactac tactgttccg    2520
tgactccatg ggtgaagtca ccaacaggtt cctggcagaa ggaggcagag atccactcca    2580
agcccgtttt tataactgtg aagatggatg tgctgaacgc cttcaagtat ccccttgctga   2640
tcggcatcgg tctgtccacg gtcatcgggc tcctgtcctg tctcatcggg tactgcagct    2700
cccactggtt ttgtaagaag gaggttcagg agacacggcg cgagcgccgc aggctcatgt    2760
cgatggagat ggactaggct ggcccgggag gggagtgaca gagggacgtt ctaggagcaa    2820
ttggggcaag aagaggacag tgatattta aaacaaagtg tgttacacta aaaaccagtc     2880
ctctctaatc tcaggtggga cttggcgctc tctctttct gcatgtcaag ttctgagcgc     2940
```

```
ggacatgttt  accagcacac  ggctcttctt  cccacggcac  tttctgatgt  aacaatcgag   3000
tgtgtgtttt  cccaactgca  gcttttaat   ggttaacctt  catctaattt  tttttctccc   3060
actggtttat  agatcctctg  acttgtgtgt  gtttatagct  tttgtttcgc  ggggttgtgg   3120
tgaggaaggg  gtgatggcat  gcggagttct  ttatcttcag  tgagaatgtg  cctgcccgcc   3180
tgagagccag  cttccgcgtt  ggaggcacgt  gttcagagag  ctgctgagcg  ccaccctcta   3240
cccggctgac  agacaacaca  gacctgtgcc  gaaggctaat  ttgtggcttt  tacgacccta   3300 ccccacccc   tgttttcagg  ggtttagact  acatttgaaa  tccaaacttg  gagtatataa   3360
cttttttttg  agcccaactg  cttttttttt  ttttttttt   gcttctctgc  ccttttcca    3420 tttcttttgt  atttgttttc  tgtgagagca  ctgaaatggc  agccctggaa  tctacaattt   3480
ggctctccac  tgagcacctt  atcttgccac  cttagcctta  agaatgaata  tgaagaaaaa   3540
tacacagcca  cctctgtcca  gggcagtaag  aagggctgca  aggaagggga  ggatggggac   3600
aaggaaagga  tcagataccT  gctccagtag  ttgtgaggcc  actgtgtctc  agggactcc    3660 aggaggagca  gaagagggat  cccacgaagt  tattcttacg  cagctggggc  caggagggtc   3720
agagtggtgc  caggtgcaag  ttaggctaaa  gaagccacca  ctattcctct  ctcttgccca   3780
ttgtgggggg  caaaggcatt  ggtcaccaag  agtcttgcag  ggggacccac  agatatgcca   3840
tgtccttcac  acgtgcttgg  gctccttaac  ctgaaggcaa  attgctactt  gcaagactga   3900
ctgacttcaa  ggaatcagaa  attacctaga  agcaccatgt  tttttctatg  accttttcag   3960
tccttcaggt  cattttaagg  tccactgcag  ggggttagtg  agaaagggta  tactttgtgg   4020
tatgttttgc  tttcctaata  gggacatgaa  ggaaacccag  caatttgctg  ttatgtgaat   4080
ggcctgtaga  gcagagtcaa  gagcggtgtg  ctttgcccga  ctgctcccat  caggaatagg   4140
agagtagaca  gagatcttcc  acatcccagg  cttctgctgc  tgctttaaaa  gctctgtcct   4200
tggagcctcc  cgctccctga  agtgtctcgc  cccctgcaca  gcactggcct  ttcggaagca   4260
tcccagtagg  gttttctgag  gctcgctggt  gactcatgcc  ctaattgcaa  tcctctgctt   4320
ttatcttgac  tttgaaggat  ctaacactgc  tctctcttcc  aaagggggaaa  aaaagattca  4380 tttgttttga  gcaataaact  aatacaaaat  gatggccatt  catgtgcagc  tctttgtcac   4440
catgggccgg  atgagttgtg  ctcctcctgg  ctcaccattt  cccctgctc   ccccacagcc   4500 ggttctgcac  ttatcaccga  gtcgcccctg  gaagcagatt  cccattgagt  tttccccacc   4560
aaggggacca  tgcacatggt  agaaacatta  gattctgcat  tgacagtagc  ctttccttgg   4620
cccgggcctg  tggtgggaag  acgggcaaca  agtataccc   accagggcct  gagtgactag   4680
aggaagagga  cgaggccttg  ttggcactag  atttgggtat  ttctgcatg   tcataacata   4740 tcctaactgc  tatttcagaa  gaggcagctt  gtaggtgatt  gtacaagtga  gaattaaaga   4800
gagaacaaat  atttaaacag  gtgctgtatt  agtaacagcc  agtgcccttt  cagcccttgc   4860
atctattaaa  aggagattca  ggattttatt  ggcacaggcc  cttcttagta  ggaagaaagg   4920
gtgcttagct  ttgacctga   ccgggtgtgt  gtaaaccat   ggactgagtc  acagcagaca   4980
ctcgatggtg  gtaaatgtga  tgggtgctta  cacactgtac  cttttccttt  catactgatg   5040
ctgcagttca  gggctggagt  tgttaaggca  ttgacctcca  cccacctgcc  ccatgtccac   5100
tgggctgccc  aagctgcatg  tcacctgagg  gctggcagga  aggggcgaga  aatcccaggg   5160
cattgtacca  aggacctagt  tccttctagg  gatataaatt  tccaggaatg  tgtatttta    5220 atgtggtgag  atgcactctt  ttgttgtacc  aaatagggct  ccccacccca  cccctgcgac   5280
aagtgctctt  ctagaacagg  ttcctaccag  cagcactggt  gtgaatgaaa  gagagaccca   5340
```

```
gccgcgtctc acacaggtgg aattgcactt cttaacaaaa aggaacttta taaaagtttg    5400
ggatttttt  tcctaatcat aaaaatagcc ccagaaagag cctaagctat gttcagatag    5460
aagcctcgaa attcctgtaa attgtttact ttatgatgtt tacatacacg tttcactttg    5520
aaaaaaaatg caaatcgact ttttaacaac tgttgagatg tttcatggga cagtagaact    5580
ctgactcacc aactgggcta aattttaatt taaaaatgta tttatttgag tgtctttccc    5640
cccctcaccc tcaccatctg aggggctccc tgagatcttg gtagaggagg ccctcctgc    5700
ccagaccttc gtttgtttcc ccggtggccc ttgcttcttg ctttgcagac tgcctgcagc    5760
catgattttg tcactgacat ctgtgagcca aagactgagc cttttggca  ggaataataa    5820
gcaatactac acaacttgct actttcagaa aacttttttt tagcttcacc gatgacaaca    5880
gaggaagaag ggaactggga tttgggtaag ttctcctcca ctgtttgacc aaattctcag    5940
tgataaatat gtgtgcagat ccctagaaga gaaaacgctg actttctttt taagtgtggc    6000
acataaggat ctgcagaatt ttccgtagac aaagaaagga tcttgtgtat ttttgtccat    6060
atccaatgtt atatgaacta attgtattgt tttatactgt gaccacaaat attatgcaat    6120
gcaccatttg tttttattt  cattaaagga agtttaattt aaaaaaaaaa aa            6172
```

```
<210> SEQ ID NO 22
<211> LENGTH: 863
<212> TYPE: PRT
<213> ORGANISM: homo sapiens

<400> SEQUENCE: 22

Met Gly Arg Leu Ala Ser Arg Pro Leu Leu Ala Leu Leu Ser Leu
1               5                   10                  15

Ala Leu Cys Arg Gly Arg Val Val Arg Val Pro Asn Val Ser Asp Tyr
            20                  25                  30

Asp Gly Pro Ser Glu Gln Asn Phe Asp Trp Ser Phe Ser Ser Leu Gly
        35                  40                  45

Ser Ser Phe Val Glu Leu Ala Ser Thr Trp Glu Val Gly Phe Pro Ala
    50                  55                  60

Gln Leu Tyr Gln Glu Arg Leu Gln Arg Gly Glu Ile Leu Leu Arg Arg
65                  70                  75                  80

Thr Ala Asn Asp Ala Val Glu Leu His Ile Lys Asn Val Gln Pro Ser
                85                  90                  95

Asp Gln Gly His Tyr Lys Cys Ser Thr Pro Ser Thr Asp Ala Thr Val
            100                 105                 110

Gln Gly Asn Tyr Glu Asp Thr Val Gln Val Lys Val Leu Ala Asp Ser
        115                 120                 125

Leu His Val Gly Pro Ser Ala Arg Pro Pro Ser Leu Ser Leu Arg
    130                 135                 140

Glu Gly Glu Pro Phe Glu Leu Arg Cys Thr Ala Ala Ser Ala Ser Pro
145                 150                 155                 160

Leu His Thr His Leu Ala Leu Leu Trp Glu Val His Arg Gly Pro Ala
                165                 170                 175

Arg Arg Ser Val Leu Ala Leu Thr His Glu Gly Arg Phe His Pro Gly
            180                 185                 190

Leu Gly Tyr Glu Gln Arg Tyr His Ser Gly Asp Val Arg Leu Asp Thr
        195                 200                 205

Val Gly Ser Asp Ala Tyr Arg Leu Ser Val Ser Arg Ala Leu Ser Ala
    210                 215                 220

Asp Gln Gly Ser Tyr Arg Cys Ile Val Ser Glu Trp Ile Ala Glu Gln
225                 230                 235                 240
```

```
Gly Asn Trp Gln Glu Ile Gln Glu Lys Ala Val Glu Ala Thr Val
            245                 250                 255

Val Ile Gln Pro Thr Val Leu Arg Ala Ala Val Pro Lys Asn Val Ser
            260                 265                 270

Val Ala Glu Gly Lys Glu Leu Asp Leu Thr Cys Asn Ile Thr Thr Asp
            275                 280                 285

Arg Ala Asp Asp Val Arg Pro Glu Val Thr Trp Ser Phe Ser Arg Met
        290                 295                 300

Pro Asp Ser Thr Leu Pro Gly Ser Arg Val Leu Ala Arg Leu Asp Arg
305                 310                 315                 320

Asp Ser Leu Val His Ser Ser Pro His Val Ala Leu Ser His Val Asp
                325                 330                 335

Ala Arg Ser Tyr His Leu Leu Val Arg Asp Val Ser Lys Glu Asn Ser
            340                 345                 350

Gly Tyr Tyr Tyr Cys His Val Ser Leu Trp Ala Pro Gly His Asn Arg
            355                 360                 365

Ser Trp His Lys Val Ala Glu Ala Val Ser Ser Pro Ala Gly Val Gly
    370                 375                 380

Val Thr Trp Leu Glu Pro Asp Tyr Gln Val Tyr Leu Asn Ala Ser Lys
385                 390                 395                 400

Val Pro Gly Phe Ala Asp Asp Pro Thr Glu Leu Ala Cys Gln Val Val
                405                 410                 415

Asp Thr Lys Ser Gly Glu Ala Asn Val Arg Phe Thr Val Ser Trp Tyr
            420                 425                 430

Tyr Arg Met Asn Arg Arg Ser Asp Asn Val Val Thr Ser Glu Leu Leu
            435                 440                 445

Ala Val Met Asp Gly Asp Trp Thr Leu Lys Tyr Gly Glu Arg Ser Lys
    450                 455                 460

Gln Arg Ala Gln Asp Gly Asp Phe Ile Phe Ser Lys Glu His Thr Asp
465                 470                 475                 480

Thr Phe Asn Phe Arg Ile Gln Arg Thr Thr Glu Glu Asp Arg Gly Asn
                485                 490                 495

Tyr Tyr Cys Val Val Ser Ala Trp Thr Lys Gln Arg Asn Asn Ser Trp
            500                 505                 510

Val Lys Ser Lys Asp Val Phe Ser Lys Pro Val Asn Ile Phe Trp Ala
    515                 520                 525

Leu Glu Asp Ser Val Leu Val Lys Ala Arg Gln Pro Lys Pro Phe
530                 535                 540

Phe Ala Ala Gly Asn Thr Phe Glu Met Thr Cys Lys Val Ser Ser Lys
545                 550                 555                 560

Asn Ile Lys Ser Pro Arg Tyr Ser Val Leu Ile Met Ala Glu Lys Pro
                565                 570                 575

Val Gly Asp Leu Ser Ser Pro Asn Glu Thr Lys Tyr Ile Ile Ser Leu
            580                 585                 590

Asp Gln Asp Ser Val Val Lys Leu Glu Asn Trp Thr Asp Ala Ser Arg
        595                 600                 605

Val Asp Gly Val Val Leu Glu Lys Val Gln Glu Asp Glu Phe Arg Tyr
    610                 615                 620

Arg Met Tyr Gln Thr Gln Val Ser Asp Ala Gly Leu Tyr Arg Cys Met
625                 630                 635                 640

Val Thr Ala Trp Ser Pro Val Arg Gly Ser Leu Trp Arg Glu Ala Ala
                645                 650                 655

Thr Ser Leu Ser Asn Pro Ile Glu Ile Asp Phe Gln Thr Ser Gly Pro
```

```
                660             665             670
Ile Phe Asn Ala Ser Val His Ser Asp Thr Pro Ser Val Ile Arg Gly
            675                 680                 685

Asp Leu Ile Lys Leu Phe Cys Ile Ile Thr Val Glu Gly Ala Ala Leu
        690                 695                 700

Asp Pro Asp Asp Met Ala Phe Asp Val Ser Trp Phe Ala Val His Ser
705                 710                 715                 720

Phe Gly Leu Asp Lys Ala Pro Val Leu Leu Ser Ser Leu Asp Arg Lys
                725                 730                 735

Gly Ile Val Thr Thr Ser Arg Arg Asp Trp Lys Ser Asp Leu Ser Leu
            740                 745                 750

Glu Arg Val Ser Val Leu Glu Phe Leu Leu Gln Val His Gly Ser Glu
        755                 760                 765

Asp Gln Asp Phe Gly Asn Tyr Tyr Cys Ser Val Thr Pro Trp Val Lys
    770                 775                 780

Ser Pro Thr Gly Ser Trp Gln Lys Glu Ala Glu Ile His Ser Lys Pro
785                 790                 795                 800

Val Phe Ile Thr Val Lys Met Asp Val Leu Asn Ala Phe Lys Tyr Pro
                805                 810                 815

Leu Leu Ile Gly Ile Gly Leu Ser Thr Val Ile Gly Leu Leu Ser Cys
            820                 825                 830

Leu Ile Gly Tyr Cys Ser Ser His Trp Cys Cys Lys Lys Glu Val Gln
        835                 840                 845

Glu Thr Arg Arg Glu Arg Arg Arg Leu Met Ser Met Glu Met Asp
    850                 855                 860

<210> SEQ ID NO 23
<211> LENGTH: 2197
<212> TYPE: DNA
<213> ORGANISM: homo sapiens
<220> FEATURE:
<221> NAME/KEY: misc_feature
<222> LOCATION: (1037)..(1037)
<223> OTHER INFORMATION: n is a, c, g, or t
<220> FEATURE:
<221> NAME/KEY: misc_feature
<222> LOCATION: (1236)..(1236)
<223> OTHER INFORMATION: n is a, c, g, or t

<400> SEQUENCE: 23
gtgcattcag acacaccatc agtaattcgg ggagatctga tcaaattgtt ctgtatcatc      60
actgtcgagg gagcagcact ggatccagat gacatggcct ttgatgtgtc ctggtttgcg     120
gtgcactctt ttggcctgga caaggctcct gtgctcctgt cttccctgga tcggaagggc     180
atcgtgacca cctcccggag ggactggaag agcgacctca gcctggagcg cgtgagtgtg     240
ctggaattct tgctgcaagt gcatggctcc gaggaccagg actttggcaa ctactactgt     300
tccgtgactc catgggtgaa gtcaccaaca ggttcctggc agaaggaggc agagatccac     360
tccaagcccg tttttataac tgtgaagatg gatgtgctga acgccttcaa gtatcccttg     420
ctgatcggcg tcggtctgtc cacggtcatc gggctcctgt cctgtctcat cgggtactgc     480
agctcccact ggtgttgtaa gaaggaggtt caggagacac ggcgcgagcg ccgcaggctc     540
atgtcgatgg agatggacta ggctggcccg gaggggagt gacagaggga cgttctagga     600
gcaattgggg caagaagagg acagtgatat ttaaaacaa agtgtgttac actaaaaacc     660
agtcctctct aatctcaggt gggacttggc gctctctctt ttctgcatgt caagttctga     720
gcgcggacat gtttaccagc acacggctct tcttcccacg gcactttctg atgtaacaat     780
```

```
cgagtgtgtg ttttcccaac tgcagctttt taatggttaa ccttcatcta attttttttc    840
tcccactggt ttatagatcc tctgacttgt gtgtgtttat agcttttgtt tcgcggggtt    900
gtggtgagga aggggtgatg gcatgcggag ttctttatct tcagtgagaa tgtgcctgcc    960
cgcctgagag ccagcttccg cgttggaggc acgtgttcag agagctgctg agcgccaccc   1020 tctaccggc tgacagncaa cacagacctg tgccgaaggc taatttgtgg cttttacgac   1080
cctaccccac cccctgtttt caggggttta gactacattt gaaatccaaa cttggagtat   1140
ataacttctt attgagccca actgcttttt tttttttttt tttttgctt ctctgcccct   1200 tttccatttc ttttgtattt gttttctgtg agagcnctga aatggcagcc ctggaatcta   1260
caatttggct ctccactgag caccttatct tgccaccta gccttaagaa tgaatatgaa   1320
gaaaaataca cagccacctc tgtccagggc agtaagaagg gctgcaagga aggggaggat   1380
ggggacaagg aaaggatcag atacctgctc cagtagttgt gaggccactg tgtctcaggg   1440
gactccagga ggagcagaag agggatccca cgaagttatt cttacgcagc tggggccagg   1500
agggtcagag tggtgccagg tgcaagttag gctaaagaag ccaccactat tcctctctct   1560
tgcccattgt gggggggcaaa ggcattggtc accaagagtc ttgcaggggg acccacagat   1620
atgccatgtc cttcacacgt gcttgggctc cttaacctga aggcaaattg ctacttgcaa   1680
gactgactga cttcaaggaa tcagaaatta cctagaagca ccatgttttt tctatgacct   1740
tttcagtcct tcaggtcatt ttaaggtcca ctgcagggg ttagtgagaa agggtatact   1800
ttgtggtatg ttttgctttc ctaataggga catgaaggaa acccagcaat ttgctgttat   1860
gtgaatggcc tgtagagcag agtcaagagc ggtgtgcttt gcccgactgc tcccatcagg   1920
aataggagag tagacagaga tcttccacat cccaggcttc tgctgctgct ttaaaagctc   1980
tgtccttgga gcctcccgct ccctgaagtg tctcgccccc tgcacagcac tggcctttcg   2040
gaagcatccc agtagggttt tctgaggctc gctggtgact catgccctaa ttgcaatcct   2100
ctgcttttat cttgactttg aaggatctaa cactgctctc tcttccaaag gggaaaaaaa   2160
gattcatttg ttttgagcaa taaactaata caaaatg                           2197
```

ANTI-TUMOR DRUG, MEDICAMENT, COMPOSITION, AND USE THEREOF

The present invention relates to the field of treatments for cancers. More specifically, the present invention relates to the treatment of cancers by small polypeptides.

Cancer is a class of diseases or disorders characterized by uncontrolled division of cells and the ability of these cells to spread, either by direct growth into adjacent tissue through invasion, or by implantation into distant sites by metastasis (where cancer cells are transported through the bloodstream or lymphatic system). Cancer may affect people at all ages, but risk tends to increase with age. It is one of the principal causes of death in developed countries.

There are many types of cancer. Severity of symptoms depends on the site and character of the malignancy and whether there is metastasis. Once diagnosed, cancer is usually treated with a combination of surgery, chemotherapy and radiotherapy. As research develops, treatments are becoming more specific for the type of cancer pathology. Drugs that target specific cancers already exist for several cancers. If untreated, cancers may eventually cause illness and death, though this is not always the case.

Current treatments target distinct properties of malignant cells, such as for example evading apoptosis, unlimited growth potential (immortalization) due to overabundance of telomerase, self-sufficiency of growth factors, insensitivity to anti-growth factors, increased cell division rate, altered ability to differentiate, no ability for contact inhibition, ability to invade neighbouring tissues, ability to build metastases at distant sites, ability to promote blood vessel growth (angiogenesis).

Tumor angiogenesis is the proliferation of a network of blood vessels that penetrates into the tumor, supplying nutrients and oxygen and removing waste products. Tumor angiogenesis actually starts with cancerous tumor cells releasing molecules that send signals to surrounding normal host tissue. This signalling activates certain genes in the host tissue that, in turn, make proteins to encourage growth of new blood vessels. Solid tumors must stimulate the formation of new blood vessels in order to obtain the nutrients and oxygen necessary for their growth, thus providing a route by which the tumors can metastasize to distant sites.

Experimental evidence has suggested that malignant tumors can induce angiogenesis through the elaboration of a variety of factors, such as acidic fibroblast growth factor (aFGF), basic fibroblast growth factor (bFGF), vascular endothelial growth factor (VEGF), platelet derived growth factor (PDGF), transforming growth factor alpha (TGF-alpha), tumor necrosis growth factor alpha (TNF-alpha), and many others (Liotta et al., 1991, *Cell* 64: 327-336; Hanahan et al., *Cell* 86: 353-364).

Nowadays, plenty of chemotherapeutic molecules targeting angiogenesis are available on the market. Well known naturally occurring angiogenesis inhibitors are angiostatin, endostatin, interferons, platelet factor 4, prolactin 16 Kd fragment, thrombospondin, TIMP-1 (tissue inhibitor of metalloprotease-1), TIMP-2 and TIMP-3. These molecules can be used as chemotherapeutic treatments, as well as other drugs such as for example combrestatin A4, EMD 121974, TNP-470, squalamine, thalidomide, interferon-alpha, anti-VEGF, antibodies . . . . However, their efficiency is never sufficient and alternative treatments are desirable.

There is therefore a need of alternative chemotherapeutic agents for the treatment of tumors, having increased efficiency, being less invasive or toxic, and resulting in an increased rate of recovery.

WO 03/080105, in the name of the Applicant, describes five genes involved in the regulation of angiogenesis. Amongst these genes, "gene 168" (SEQ ID No 1 in this specification), which encodes "protein 168A" (SEQ ID No 2 in this specification), has been described as implied in the activation of angiogenesis. In particular, WO 03/080105 discloses that protein 168A is expressed in endothelial cells stimulated with pro-angiogenic factors, such as for example TNF-α. WO 03/080105 also describes that the expression, in human endothelial cells, of an antisens sequence of gene 168, i.e. the inhibition of the expression of gene 168, inhibits the formation of capillary tubes.

In silico experiments further revealed that protein 168A, which is constituted of 924 aminoacids, may have a single transmembrane domain, and five Immunoglobulin-like domains.

Going deeper in their researches, the inventors produced truncated forms of protein 168A, corresponding to various fragments of protein 168A. Amongst these fragments, 168A-T2 corresponds to a fragment of the extracellular domain of protein 168A, and is identified by SEQ ID NO:4 in this specification (108 amino acids).

In a first experiment, the inventors found that protein 168A-T2 may inhibit human endothelial cell proliferation in vitro in a dose dependent manner.

Then, in a second experiment, the inventors surprisingly found that 168A-T2 may have a strong activity to inhibit capillary tube formation in vitro, in a dose dependent manner.

Other experiments conducted by the inventors suggested that 168A-T2 may induce the inhibition of the migration of endothelial cells in vitro, in a dose dependent manner.

The results of the dose-response study further revealed that the protein 168A-T2 may inhibit in a dose-dependent manner the proliferation of human endothelial cells, and this inhibition could reach more than 80% with a concentration of 3.1 µM. This tends to demonstrate that the recombinant protein may be a potent anti-angiogenic compound, at least 600-fold more potent than the anti-VEGF mAb and/or VEGF receptor (KDR)-based identified peptides (Binetruy-Tournaire R et al., Identification of a peptide blocking vascular endothelial growth factor (VEGF)-mediated angiogenesis, *EMBO J.* 2000; 19: 1525-1533).

Capillary tube formation, human endothelial cell proliferation and human endothelial cell migration are three essential steps of angiogenesis. Consequently, the fact that 168A-T2 may inhibit in vitro capillary tube formation, human endothelial cell proliferation and/or migration in a dose-dependant manner, thus constituted a strong evidence of the potent anti-angiogenic activity of the truncated forms of protein 168A.

All these results were absolutely unexpected since native protein 168A is preferably expressed in pro-angiogenic conditions, i.e. in the presence of TNFα, and that the expression of an antisens of the gene 168, i.e. the inhibition of gene 168, in human endothelial cells inhibits the formation of capillary tubes. It was therefore really surprising that a truncated form of protein 168A, may have anti-angiogenic activity.

Still surprisingly, the inventors found that protein 168A-T2 had a strong anti-tumor activity in vivo, and a strong synergistic activity in combination with other chemotherapeutic agent such as for example cisplatin.

Inventors found that the test substance 168A-T2 was not toxic in Nude mice bearing tumors at different tested doses. Moreover, 168A-T2 exhibited a strong statistically significant anti-tumoral activity against human tumors as early as two days after the beginning of the treatment. This anti-tumoral activity was persistent during the treatment period. This anti-tumoral effect of 168A-T2 represented a realistic therapeutic approach as a monotherapy. Its efficacy was also strongly potentiated when combined with the cytotoxic anticancer drug CDDP (Cisplatin), which suppressed tumor growth. Cisplatin alone, on the other hand, did not eradicate tumor growth.

The data strongly suggested that 168A-T2 may be of use either as a primary anti-tumoral agent or as an add-on synergic therapy to primary cytotoxic agents for the treatment of cancers.

As mentioned above, it is now established that protein 168A is expressed in endothelial cells, and that its expression is enhanced when angiogenesis is stimulated by pro-angiogenic factors such as TNFα, as described in WO03/080105. Protein 168A is a transmembrane protein, and might be implied in the transduction of a pro-angiogenic signal. Without wanting to be bound with a theory, Applicants suggest that the truncated forms of 168A may play their role through a "soluble receptor mechanism": truncated forms of 168A may remain soluble on the surface of the cell and may be recognized by the ligand of the native 168A protein. As a result, there may be a competition in the recognition of the ligand between the soluble forms of 168A (the fragments of the invention) and the native transmembrane protein, and consequently a decrease, in a dose dependent manner, of the transduction of the pro-angiogenic signal, therefore resulting in the inhibition of angiogenesis and then in the decrease of tumour volume.

The invention thus relates, in a first aspect, to a nucleic acid having the nucleic acid sequence of SEQ ID NO:3, or having at least 50%, preferably 70%, more preferably 90% identity with the nucleic acid sequence of SEQ ID NO:3, or fragments thereof having at least 60 contiguous nucleotides, or nucleic acid sequences having at least 50%, preferably 70%, more preferably 90% identity with the nucleic acid sequence of said fragments, provided that said nucleic acid is not SEQ ID NO:1, SEQ ID NO: 21, SEQ ID NO: 58 disclosed in US2005/106644 or SEQ ID NO: 23, said nucleic acid coding for a polypeptide or peptide having anti-angiogenic and anti-tumour activity.

SEQ ID NO: 21 corresponds to the nucleic acid sequence SEQ ID NO: 87 disclosed in WO02/081731.

SEQ ID NO: 23 corresponds to the nucleic acid sequence SEQ ID NO: 28 disclosed in WO03/080105.

In a preferred embodiment, the invention relates to the nucleic acid sequence SEQ ID NO: 3 or a nucleic acid sequence called here for practical reason SEQ ID NO X which, when aligned with SEQ ID N: 3, has:

a) a percentage of identical residues over SEQ ID NO: 3 length of at least 50%, preferably of at least 70% and more preferably of at least 90% and b) a percentage of identical residues over said amino acid sequence SEQ ID NO X length of at least 80%, preferably of at least 90% and more preferably of at least 95%, or fragments thereof having at least 60 contiguous nucleotides.

According to the invention, the percentage of identical residues over SEQ ID NO: 3 length corresponds to the number of identical residues between SEQ ID NO: X and SEQ ID NO: 3 divided by the number of residues in SEQ ID NO: 3. When using GenomeQuest database, said percentage of identical residues over SEQ ID NO:3 length corresponds to query percentage identity (% id Query), where query is SEQ ID NO:3.

According to the invention, the percentage of identical residues over SEQ ID NO: X length corresponds to the number of identical residues between SEQ ID NO: X and SEQ ID NO: 3 divided by the number of residues in SEQ ID NO: X. When using GenomeQuest database, said percentage of identical residues over SEQ ID NO: X length corresponds to subject percentage identity (% id Subject).

As used above, "fragments" means truncated sequences of SEQ ID NO:3, having at least 60 contiguous nucleotides, and coding for an active peptide or polypeptide having an anti-angiogenic and anti-tumour activity. In a particular embodiment, the fragments have the nucleic acid sequence of SEQ ID NO:13, SEQ ID:14, SEQ ID NO:15, SEQ ID NO:16, SEQ ID NO:17, or SEQ ID NO:18. In another embodiment, the invention also encompasses nucleic acid fragments, which when aligned with fragments of SEQ ID NO: 3 of at least 60 contiguous nucleotides and in particular SEQ ID NO: 13, 14, 15, 16, 17 or 18, have a) a percentage of identical residues over the length of said fragments of SEQ ID NO: 3 of at least 50%, preferably of at least 70% and more preferably of at least 90% and b) a percentage of identical residues over said nucleic acid fragments length of at least 65%, preferably of at least 70% and more preferably of at least 90%, and encoding a peptide having an anti-angiogenic and anti-tumour activity.

In another aspect, the invention relates to an expression vector comprising at least one nucleic acid sequence as defined above.

As used herein, "expression vector" means any plasmid or nucleic acid construct, which is used to introduce and express a specific nucleic acid sequence into a target cell.

The invention further relates, in a third aspect, to an active polypeptide comprising the amino acid sequence of SEQ ID NO:4, or having at least 50%, preferably 70%, more preferably 90% identity with the amino acid sequence of SEQ ID NO:4, or fragments thereof having at least 20 contiguous amino acids, or peptides having at least 50%, preferably 70%, more preferably 90% identity with the amino acid sequence of said fragments, provided that said polypeptide is not SEQ ID NO:2, SEQ ID NO:22, or the polypeptide encoded by SEQ ID NO: 58 disclosed in US2005/106644 or encoded by SEQ ID NO: 23.

SEQ ID NO: 22 corresponds to the amino acids sequence SEQ ID NO: 87 disclosed in WO02/081731.

In a preferred embodiment, the invention relates to the active polypeptide SEQ ID NO:4, or an amino acid sequence SEQ ID NO Y which, when aligned with SEQ ID N: 4, has:

a) a percentage of identical residues over SEQ ID NO: 4 length of at least 50%, preferably of at least 70% and more preferably of at least 90% and b) a percentage of identical residues over said amino acid sequence SEQ ID NO Y length of at least 65%, preferably of at least 70% and more preferably of at least 90%, or fragments thereof having at least 20 contiguous amino acids.

As used herein, "peptide" means short molecules formed from the linking, in a defined order, of less than 100 amino acids.

As used herein, "polypeptide" means molecules formed from the linking, in a defined order, of at least 100 amino acids.

As used herein, "active polypeptide" means polypeptides which have a biological activity. In the present invention the polypeptides have an anti angiogenic and anti tumour activity.

According to the invention, the polypeptide as described above has an anti-tumour activity.

According to the invention, the percentage of identical residues over SEQ ID NO: 4 length corresponds to the number of identical residues between SEQ ID NO: Y and SEQ ID NO: 4 divided by the number of residues in SEQ ID NO: 4.

When using GenomeQuest database, said percentage of identical residues over SEQ ID NO:4 length corresponds to query percentage identity (% id Query), where query is SEQ ID NO:4.

According to the invention, the percentage of identical residues over SEQ ID NO: Y length corresponds to the number of identical residues between SEQ ID NO: Y and SEQ ID NO: 4 divided by the number of residues in SEQ ID NO: Y. When using GenomeQuest database, said percentage of identical residues over SEQ ID NO:Y length corresponds to subject percentage identity (% id Subject).

According to the invention, the fragments of SEQ ID NO:4 as described above correspond to truncated forms of SEQ ID NO:4, and have an anti-tumor activity. Said fragments preferably have an amino acid sequence of at least 20 contiguous amino acids of SEQ ID NO:4. In a particular embodiment, the fragments have an amino acid sequence of at least 37 contiguous amino acids. In another particular embodiment, said fragments have the amino acid sequence of SEQ ID N:7 (90 amino acids), SEQ ID N:8 (77 amino acids), SEQ ID N:9 (66 amino acids), SEQ ID N:10 (51 amino acids), SEQ ID N:11 (37 amino acids) or SEQ ID N:12 (20 amino acids). In another embodiment, the invention also encompasses peptides, which when aligned with fragments of SEQ ID NO: 4 of at least 20 contiguous amino acids and in particular SEQ ID NO: 7, 8, 9, 10, 11 or 12, have a) a percentage of identical residues over the length of said fragments of SEQ ID NO: 4 of at least 50%, preferably of at least 70% and more preferably of at least 90% and b) a percentage of identical residues over said peptide length of at least 65%, preferably of at least 70% and more preferably of at least 90%, and having an anti-tumor activity.

In a particular embodiment, the active polypeptides according to the invention are produced by the expression vector as defined above.

In a fourth aspect, the present invention relates to a medicament comprising at least one nucleic acid sequence, vector, or polypeptide as described above.

In a fifth aspect, the invention relates to a pharmaceutical composition comprising at least one nucleic acid sequence, vector, or polypeptide as described above, and one or more pharmaceutically acceptable excipients.

In a sixth aspect, the invention relates to a pharmaceutical composition comprising at least one nucleic acid sequence, vector, or polypeptide as described above, and one or more pharmaceutically-acceptable excipients, for use in a method of treatment of cancer and/or tumors of the human or animal body.

In a particular embodiment, the pharmaceutical compositions as described above further comprise at least one another active substance selected from anti-angiogenic substances or anti-tumor substances. These substances may be chosen by the man in the art, regarding the effect to be achieved. Preferably, these substances can be selected from cisplatin, carboplatin, etoposide, ifosfamide, mitomycin, vinblastine, vinorelbine, gemcitabine, paclitaxel, docetaxel, and irinotecan, etc. . . . .

In a seventh aspect, the invention relates to a pharmaceutical composition comprising effective amounts of a polypeptide, a fragment, and/or a peptide as described above, and a platinum complex selected from the group consisting of cisplatin and carboplatin.

Applicants surprisingly found that the combination of a polypeptide according to the invention with a platinum complex showed synergistic activity.

By "synergistic", it is meant, within the present invention, that the total effect of the combination of active principles is greater than the effect of each active principle taken separately.

The medicament or composition useful in the practice of this invention is administered to the mammal by known conventional routes. The medicament or composition described herein may be administered by the same route, or by different routes. For example, the medicament or composition may be administered to patients orally or parenterally (intravenously, subcutaneously, intramuscularly, intraspinally, intraperitoneally, and the like).

When administered parenterally, the composition is preferably formulated in a unit dosage injectable form (solution, suspension, emulsion) with at least one pharmaceutically acceptable excipient. Such excipients are typically nontoxic and non-therapeutic. Examples of such excipients are water, aqueous vehicles such as saline, Ringer's solution, dextrose solution, and Hank's solution and non-aqueous vehicles such as fixed oils (e.g., corn, cottonseed, peanut and sesame), ethyl oleate, and isopropyl myristate. Sterile saline is a preferred excipient. The excipient may contain minor amounts of additives such as substances that enhance solubility, isotonicity, and chemical stability, e.g., antioxidants, buffers, and preservatives. When administered orally (or rectally) the compounds will usually be formulated into a unit dosage form such as a table, capsule, suppository, or cachet. Such formulations typically include a solid, semi-solid or liquid carrier or diluent. Exemplary diluents and excipients are lactose, dextrose, sucrose, sorbitol, mannitol, starches, gum acacia, calcium phosphate, mineral oil, cocoa butter, oil of theobroma, alginates, tragacanth, gelatin, methylcellulose, polyoxyethylene, sorbitan monolaurate, methyl hydroxybenzoate, propyl hydroxybenzoate, talc and magnesium stearate. In preferred embodiments, the pharmaceutical composition according to the invention is administered intravenously.

According to the invention, the amount of polypeptide present in the medicament or composition is effective to treat susceptible tumors. Preferably, the polypeptide is present in an amount from 0.01 to 90% in weight, preferably from 0.1% to 10% in weight, more preferably from 1% to 5% in weight, in the medicament or in the composition. These amounts are routinely adaptable by the man in the art, who is able to choose the best quantity to administer to a patient to achieve recovery.

In an eight aspect, the invention relates to the use of at least one nucleic acid sequence, vector, or polypeptide as described above, or of the medicament as described above, or of the pharmaceutical composition as described above, for the treatment of cancers and/or tumors.

According to the invention, the tumors to be treated are preferably solid tumors. More preferably, the tumors to be treated are selected from sarcomas, carcinomas, and lymphomas. Examples of such tumors are bladder cancer, melanoma, breast cancer, non-Hodgkin's lymphoma, brain cancer, bone cancer, colon and rectal cancer, liver cancer, pancreatic cancer, endometrial cancer, prostate cancer, kidney cancer, skin cancer (non-melanoma), thyroid cancer, lung cancer (small cell lung cancer and non small cell lung cancer).

In a ninth aspect, the present invention relates to a method of treatment comprising administering to a subject in need of treatment at least one nucleic acid sequence, vector, or polypeptide as described above, or the medicament as described above, or the pharmaceutical composition as described above, in an amount sufficient to inhibit cancer or tumor growth.

As used herein, "subject in need of treatment" means any human or warm blood animal who suffers from cancer or tumour.

In a particular embodiment, the invention relates to the method of treatment as described above further comprising administering at least one other anti-neoplastic or anti-tumor drug.

In these methods, administering comprises topical administration, oral administration, intravenous administration, or intraperitoneal administration.

In an eight aspect, the present invention relates to a method of treatment comprising administering to a subject in need of treatment an effective amount of a polypeptide, a fragment, and/or a peptide as described above, and a platinum complex selected from the group consisting of cisplatin and carboplatin, which is sufficient to inhibit cancer or tumor growth.

Applicants surprisingly found that the administration of both a polypeptide according to the invention and a platinum complex showed synergistic effect.

In one embodiment, said polypeptide or fragments thereof and said platinum complex are administered simultaneously.

In another embodiment, said polypeptide or fragments thereof and said platinum complex are administered sequentially. Preferably, said polypeptide or fragments thereof and said platinum complex are administered by separate routes, i.e. orally or parenterally (intravenously, subcutaneously, intramuscularly, intraspinally, intraperitoneally, and the like).

In a particular embodiment, said platinum complex is cisplatin.

In another particular embodiment said platinum complex is carboplatin.

The present invention will now be further described with reference to the following non-limiting examples.

FIG. 2a: Control (Buffer Urea 2M)
FIG. 2b: 168A-T2 3.5 µg/mL (0.2 µM)
FIG. 2c: 168A-T2 6.9 µg/mL (0.4 µM)
FIG. 2d: 168A-T2 13.6 µg/mL (0.8 µM)

FIG. 3a: Control (Buffer Urea 2M)
FIG. 3b: 168A-T2 12 µg/mL (0.7 µM)
FIG. 3c: 168A-T2 17 µg/mL (1 µM)
FIG. 3d: 168A-T3 23 µg/mL (1.35 µM)

Figure 1:
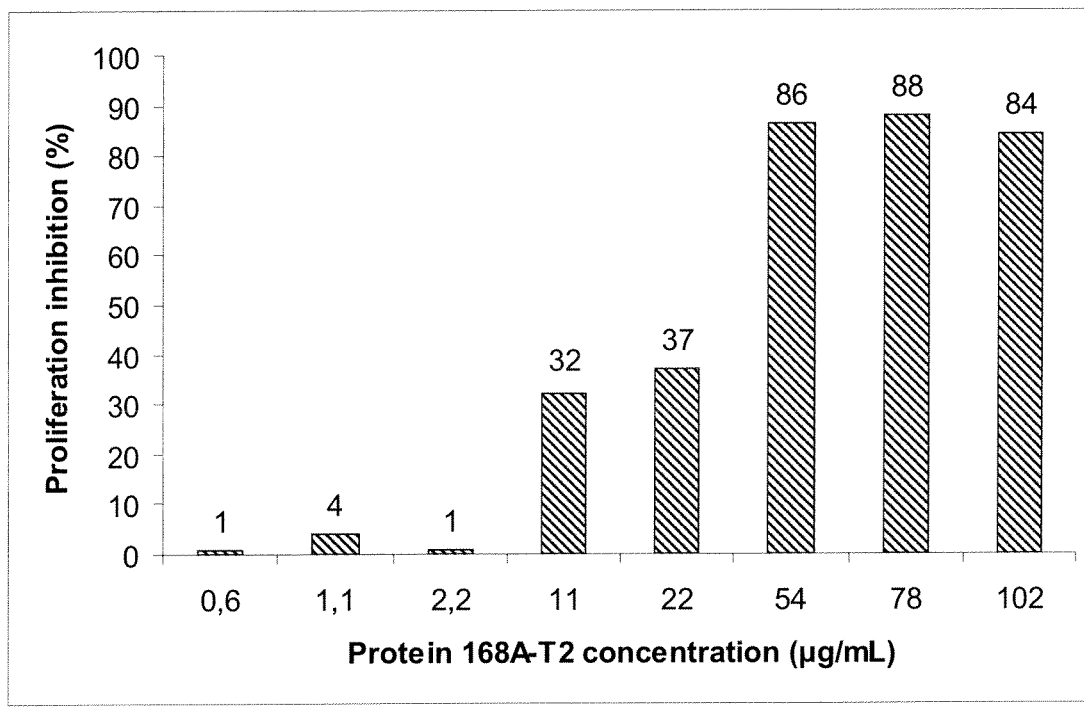
FIG. 1 is a diagram representing the % inhibition of endothelial cell proliferation in vitro with increasing concentrations of protein 168A-T2.

SEQ ID NO:1 corresponds to the nucleic acid sequence of gene 168.

SEQ ID NO:2 corresponds to the amino acid sequence of protein 168A.

SEQ ID NO:3 corresponds to the nucleic acid sequence of 168A-T2.

SEQ ID NO:4 corresponds to the amino acid sequence of 168A-T2.

SEQ ID NO:5 corresponds to the nucleic acid sequence of 168A-T2 within vector pET30.

SEQ ID NO:6 corresponds to the amino acid sequence of 168A-T2 as produced with the vector pET30.

SEQ ID NO:7 corresponds to the amino acid sequence of a fragment of 168A-T2.

SEQ ID NO:8 corresponds to the amino acid sequence of a fragment of 168A-T2.

SEQ ID NO:9 corresponds to the amino acid sequence of a fragment of 168A-T2.

SEQ ID NO:10 corresponds to the amino acid sequence of a fragment of 168A-T2.

SEQ ID NO:11 corresponds to the amino acid sequence of a fragment of 168A-T2.

SEQ ID NO:12 corresponds to the amino acid sequence of a fragment of 168A-T2.

SEQ ID NO:13 corresponds to the nucleic acid sequence coding for SEQ ID NO:7.

SEQ ID NO:14 corresponds to the nucleic acid sequence coding for SEQ ID NO:8.

SEQ ID NO:15 corresponds to the nucleic acid sequence coding for SEQ ID NO:9.

SEQ ID NO:16 corresponds to the nucleic acid sequence coding for SEQ ID NO:10.

SEQ ID NO:17 corresponds to the nucleic acid sequence coding for SEQ ID NO:11.

SEQ ID NO:18 corresponds to the nucleic acid sequence coding for SEQ ID NO:12.

SEQ ID NO:19 corresponds to the nucleic acid sequence of primer CDS5.

SEQ ID NO:20 corresponds to the nucleic acid sequence of primer CDS4.

EXAMPLE 1

Production of Protein 168A-T2

Synthesis of Insert 168A-T2:

First, gene 168A was cloned in pGEM®-T easy vector system (Promega®) according to known procedures (the vector obtained was called "pGEM-T-168A").

Second, the insert T2 (SEQ ID NO:3), coding for the plasma membrane adjacent part of the extra-cellular domain of the protein 168A, was amplified by PCR using the plasmid "pGEM-T-168A" and the two primers CDS5 (SEQ ID NO:19) and CDS4 (SEQ ID NO:20) (table 1).

TABLE 1

| Primer | SEQ ID NO | Sequence |
|---|---|---|
| 168A-cds-5 | 19 | GACGACGACAAGATGGCCTTTGATGTGTCCTGGTTTG |
| 168A-cds-4 | 20 | GAGGAGAAGCCCGGTTCAGGGATACTTGAAGGCGTTCAGCACA |

Third, the DNA sequence (SEQ ID NO:3) coding for the protein 168A-T2 was inserted into the vector pET-30 EK/LIC (Novagen®) according to known procedures (pET-30-168A-T2). The nucleic acid sequence coding for 168A-T2 within the pET-30 vector is given in SEQ ID NO:5.

The purified vector was then introduced in *E. coli* BL21 (DE3)pLys for protein production. Colonies were controlled for the presence of both the vector end the insert by PCR.

The size of the produced protein 168A-T2 was 18 kD, which corresponded to the expected size, comprising the His-Tag at the N-terminal as confirmed by sequencing. The amino acid sequence of the protein 168A-T2 as produced is given in SEQ ID NO:6.

Extraction and Purification of the Protein 168A-T2

As the protein 168A-T2 was produced within the insoluble fraction of the bacteria, it necessitated an extraction in denaturating conditions Following culture, bacteria were lyzed, centrifuged and the supernatant discarded. The insoluble fraction obtained was treated with Tris-HCl 20 mM, urea 8 M, imidazol 5 mM, NaCl 0.5 M, GSH 5 mM, pH 8.0. After this treatment, the suspension was centrifuged and the supernatant collected, filtered on 0.45 μm membranes to discard insoluble materials. The filtered extract was then used to purify the protein 168A-T2 by using a His-Trap column (Amersham®) connected to a HPLC system (Amersham).

The purified protein obtained was diluted in 4 M urea and 0.3 M imidazol. To remove these agents from the preparation, the solution was subjected to dialysis at 4° C.

Following these steps of dialysis, the purified protein was centrifuged at 4,000×g for 15 min and filtered on 0.45 μm membranes to eliminate possible precipitates. The purified protein preparation was controlled for protein content according to the method described by Bradford in 1976 (Anal. Biochem. 72:248-54) and by SDS-PAGE. The gels were analyzed using the Gene Genius software to quantify the purity by image analysis.

To increase purity of the protein 168A-T2, we performed a second purification step by using ion exchange liquid chromatography. The HisTrap purified preparation was diluted 3 times with the buffer Tris-HCl 20 mM, pH 8, 2 M urea (to decrease the concentration of NaCl to 50 mM), and loaded on MonoS column connected to a HPLC system run by Unicorn software (Amersham, GE, Saclay, France). The column was then washed extensively and eluted with a linear gradient of ionic force (0.05 M to 0.5 M NaCl in the Tris-HCl 20 mM buffer, pH 8, 2 M urea). The purified protein preparation was controlled for protein content both by Bradford and by SDS-PAGE.

EXAMPLE 2

Test of Inhibition of Endothelial Cell Proliferation by 168A-T2 In Vitro

HUVEC cells were cultured to confluency in complete EGM2-MV medium (Cambrex) at 37° C. and in 5% $CO_2$ humidified atmosphere. Cells were then collected by trypsine-EDTA digestion (Versene, Eurobio). After 5 min, the enzymatic reaction was stopped by adding 3 ml of the culture medium containing 5% FCS. Cells were then centrifuged at 220 g for 10 min at room temperature, washed twice with 5 ml of culture medium, suspended in complete culture medium, counted and adjusted to 50 000 cells/ml. One hundred μL per well were then distributed to a 96-well cell culture grade micro-plate (5 000 cells/well) and incubated with different concentrations of the purified protein 168A-T2 in Tris-HCl 20 mM buffer (pH 8), containing 150 mM NaCl and urea 2M; this buffer was used as control.

After 42 hrs at 37° C., cell proliferation was measured using thiazolyl blue tetrazolium bromide (MTT) method. Briefly, MTT (Sigma) was dissolved in PBS at 5 mg/ml, the solution was filtered (0.22 μm) and 10 μl were added to each well of the 96-well micro-plates. After 3 hrs of incubation at 37° C., 5% $CO_2$ humidified atmosphere, the micro-plates were centrifuged at 220×g for 10 min, the supernatant was discarded, and the crystals dissolved by the addition of 100 μl of DMSO to each well. The optical density (OD) at 570 nm was then measured using μQuant micro-plate reader (Bio-Tek Instrument gmbh, Colmar, France) coupled to the KC4 (Bio-Tek) software. The OD was corrected by subtracting blank-well CD values (the OD values obtained from wells without cells), and the inhibition of cell proliferation was measured relative to control (OD obtained from wells with untreated HUVEC representing the maximal proliferative response, i.e. 100%).

As shown in FIG. 1, protein 168A-T2 inhibited human endothelial cell proliferation in a dose dependent manner. This inhibition represented 80% at 54 μg/mL (i.e. 3.1 μM) of protein 168A-T2.

EXAMPLE 3

Inhibition of In Vitro Angiogenesis by 168A-T2

The purified proteins 168A-T2 was tested in vitro on angiogenesis of HUVEC induced by FGF2 and VEGF on Matrigel.

Figure 2A:
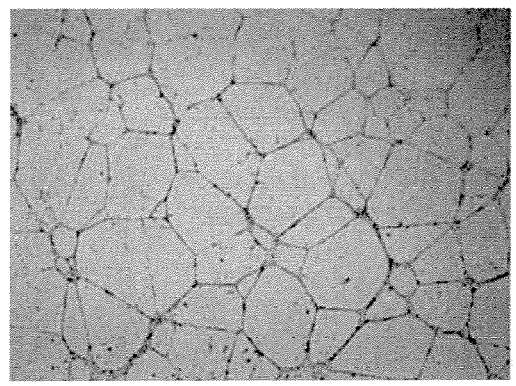
FIGS. 2a, 2b, 2c and 2d are pictures of in vitro angiogenesis of endothelial cells in different conditions.

24 wells plates were prepared with 250 μL of BD Matrigel™/well and then incubated 30 minutes in incubator. HUVEC cells were then prepared as described in example 2 and 70 000 cells (in 0.5 mL) were seeded per well and incubated with different concentrations of the purified protein 168A-T2, in Tris-HCl 20 mM buffer (pH 8), containing 150 mM NaCl and urea 2M; this buffer was used as control:

FIG. 2a: Control (Buffer Urea 2M)

Figure 2B:
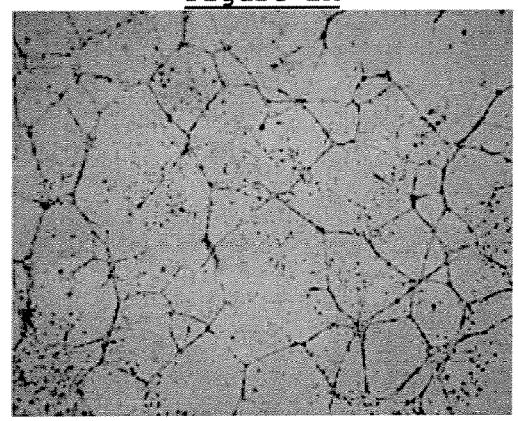
Figure 2C:
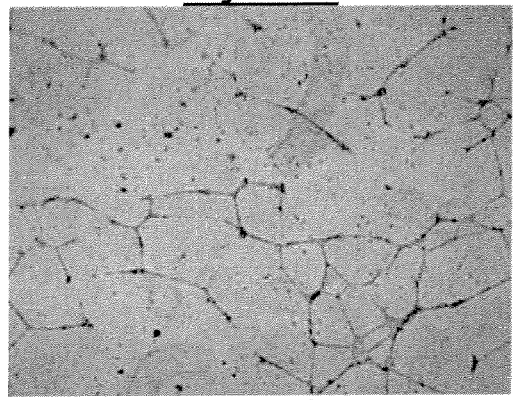
Figure 2D:
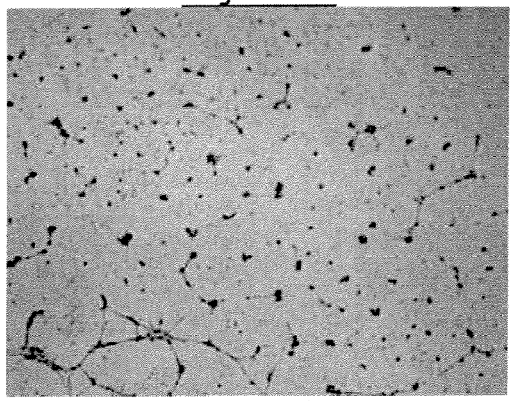

As shown in FIGS. 2b, 2c, and 2d, protein 168A-T2 inhibited in vitro angiogenesis in a dose-dependent manner.

EXAMPLE 4

Inhibition of the Migration of Human Endothelial Cells by 168A-T2

Figure 3A:
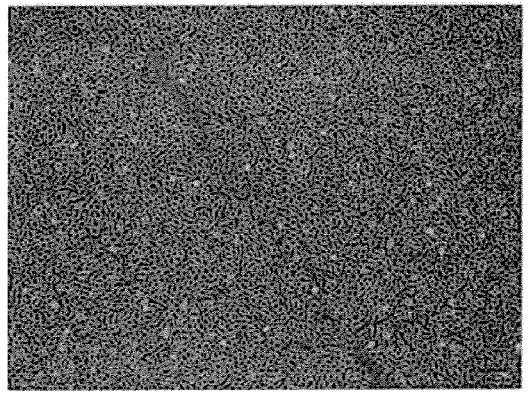
FIGS. 3a, 3b, 3c and 3d are pictures of wound assay on endothelial cells performed in different conditions.

Cell migration was tested by the wound assay described by Sato and Rifkin (J Cell Biol. 1988; 107:1199) with few modifications. HUVEC grown in growth medium EGM-2MV (Cambrex) were seeded in 24-well plates at 80 000 cells per well in 500 μL of growth medium and grown to confluence at 37° C. in a humidified atmosphere containing 5% $CO_2$. Cells were scrapped with a plastic tip on one line only. After wounding, the culture medium was changed for fresh medium (control, FIG. 3a) or fresh medium supplemented with:

After 18 hours of culture, cells were observed and photographed under the inverted microscope (Analysis, Olympus, Rungis, France).

Figure 3B:
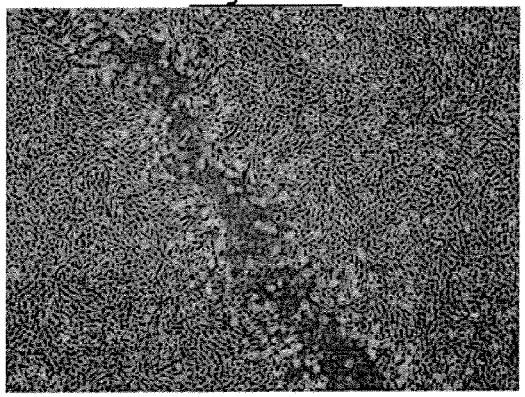
Figure 3C:
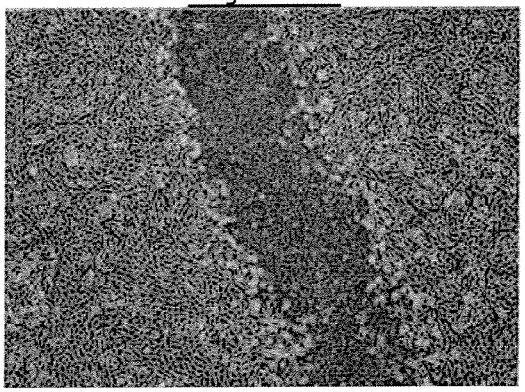
Figure 3D:
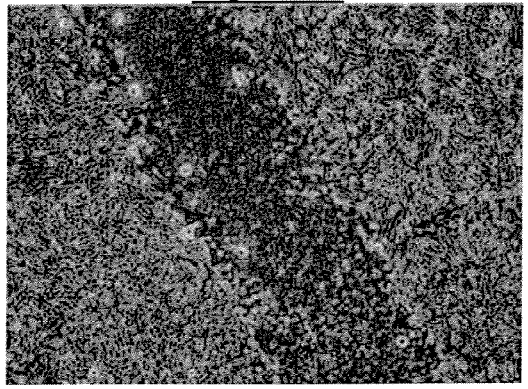

As shown in FIGS. 3b, 3c and 3d, protein 168A-T2 inhibited human endothelial cells migration in a dose dependent manner.

EXAMPLE 5

Test of Inhibition of a Kidney Cancer Cell Line Proliferation by 168A-T2 In Vitro BizX cell preparation of 50000 cells/mL was prepared in complete medium. In a 96 wells plate, 100 mL of the cell preparation was distributed in each well and then incubated with different concentrations of 168A-T2 (each concentration was tested in triplicate). After 48 hours of incubation at 37° C., 10 mL of MTT (5 mg/L in water) were added in each well. After 3 hours of incubation at 37° C., the culture medium was eliminated and 100 mL of DMSO were added to solubilize MMT crystals. The optical density (OD) at 570 nm was then measured using µQuant micro-plate reader (Bio-Tek Instrument gmbh, Colmar, France) coupled to the KC4 (Bio-Tek) software. The OD was corrected by subtracting blank-well OD values (the OD values obtained from wells without cells), and the inhibition of cell proliferation was measured relative to control (OD obtained from wells with untreated kidney tumor cells representing the maximal proliferative response, i.e. 100%).

Figure 4:
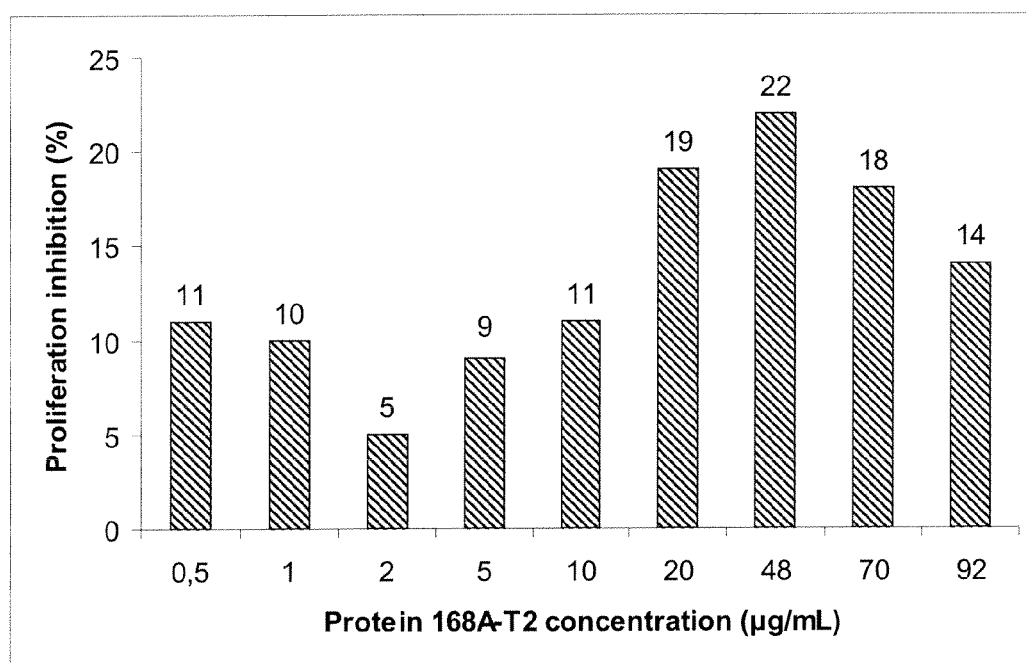
FIG. 4 is a diagram representing the % inhibition of kidney tumor cell (Biz) proliferation in vitro with increasing concentrations of protein 168A-T2.

As shown in FIG. 4, protein 168A-T2 inhibited up to 20% of proliferation of a kidney cancer line (BizX).

EXAMPLE 6

Test of Inhibition of a Lung Cancer Cell Line Proliferation by 168A-T2 In Vitro

Calu6 cells were cultured and treated as described in example 5.

Figure 5:
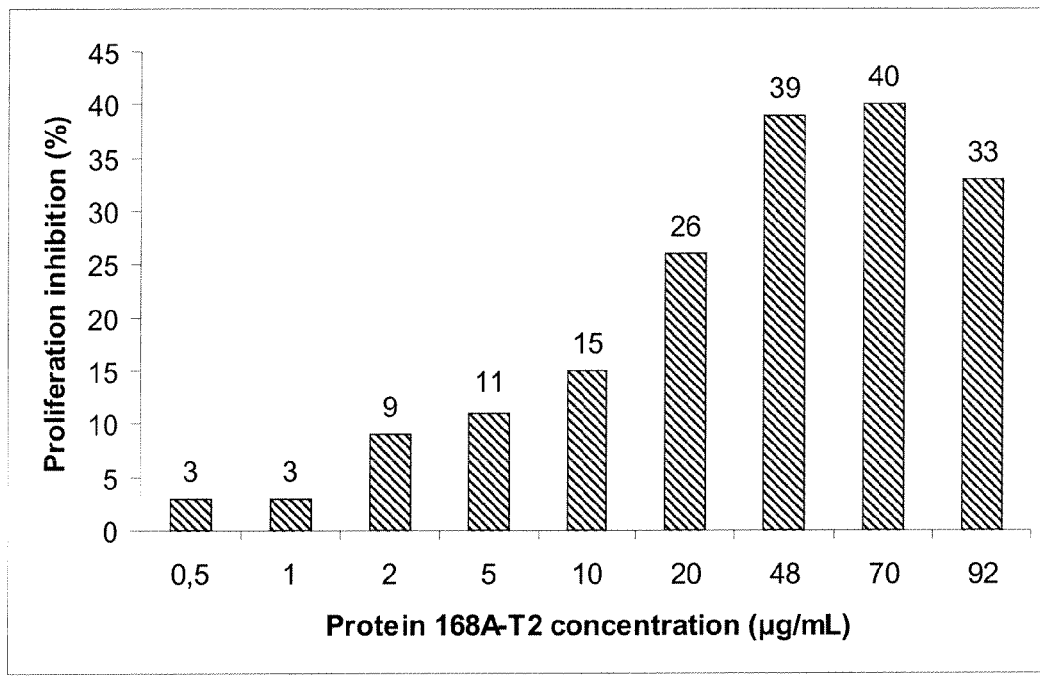
FIG. 5 is a diagram representing the % inhibition of lung tumor cell (Calu-6) proliferation in vitro with increasing concentrations of protein 168A-T2.

As shown in FIG. 5, protein 168A-T2 inhibited up to 40% of proliferation of a lung cancer line (Calu6).

EXAMPLE 7

Expression of Protein 168A in Tumor Samples

A number of different human tumor samples were screened for the expression of the gene 168A. For each pathological sample, the periphery of the tumor was separated from the core of the tumor, and the expression of the gene 168A in these two area was compared after mRNA extraction followed by RT-PCR.

Kidney Tumor Samples 19 pathological biopsies from kidney tumors were analyzed. In 11 out of 19 patients, the expression of 168A was much higher in the core than in the periphery of the tumor. In 8 patients out of 19 patients, the expression of 168A was much higher in the periphery of the tumor than in the core.

Lung Tumor Samples 40 pathological biopsies from human lung tumors were analyzed. In 23 out of 40 patients, the expression of 168A was much higher in the core than in the periphery of the tumor.

Colon Tumor Samples 33 pathological biopsies from human colon tumors were analyzed. In 13 out of 33 patients, the expression of 168A was much higher in the periphery than in the core of the tumor.

EXAMPLE 8

Test of 168A-T2 on Human Non-Small Cell Lung Cancer (CALU-6) Xenograft Model in Swiss Nude Mice In Vivo Preparation of CALU-6 Cells CALU-6 cells were cultured as adherent cells in complete EMEM medium (Ref. CM1MEM18-01, batch No. 462502, Eurobio, France) 10% fetal calf serum (FCS; Ref. CVFSVF00-01, batch No. S13021, Eurobio, France) under a 37° C., 5% $CO_2$ humidified atmosphere. They were amplified in 75 $cm^2$-flasks to reach $90 \times 10^6$ cells.

At D0, CALU-6 cells (human lung carcinoma) were collected from 75 $cm^2$-flasks by removing the medium and adding 3 ml of trypsine-EDTA (Ref. CEZTDA00-0U, batch No. 633920, Eurobio, France). After 5 min of incubation at 37° C., cells had detached from the plastic and the enzymatic reaction was stopped by adding 3 ml of EMEM medium containing 10% fetal calf serum. Cells were then centrifuged at 700 g for 5 min at room temperature. They were resuspended in serum-free EMEM culture medium. Cells were counted and viability assessment by Trypan Blue exclusion (Ref. CSTCOL03-OU, batch No. 434511, Eurobio, France). The number of viable CALU-6 cells was >99%. The number of cells was then adjusted to $25 \times 10^6$ cells/ml in serum-free medium.

Tumor Induction

Thirty healthy female Swiss Nude mice were anesthetized by IP injection of Ketamine-Xylazine (80 mg/kg-12 mg/kg; Ref. K-113, Sigma, France). CALU-6 cells $5 \times 10^6$ cells/mouse in 200 µl of serum-free medium) were then implanted subcutaneously in the right flank of each mouse. Mice were observed for 2 h post-implantation.

Treatment Schedule

At D12 post-implantation of the CALU-6 cells, the thirty mice were randomized into four groups of 5 mice. Tumor volumes had reached 54 to 296 $mm^3$ and mean tumor volumes were not statistically different between groups after randomization.

The treatment schedule, starting D12 and ending D28, is summarized in Table 2.

Animals of group 1 were treated with the vehicle solution (Tris-HCl pH 7.5, 2M Urea, 150 mM NaCl, 0.1 mM $CaCl_2$)

Animals of group 2 were treated with a solution of cisplatin in physiological serum at a concentration of 0.5 mg/mL (CDDP, cis-diamineplatinum(II) dichloride, Ref. P4394, batch No. 014K0993, Sigma, France, purity 100%, MW. 300), Animals of group 3 were treated with the vehicle supplemented with the test substance 168A-T2 at a dose of 15 mg/kg.

Animals of group 4 were treated with the vehicle supplemented with the test substance 168A-T2 at a dose of 15 mg/kg, and further received 5 mg/kg of CDDP.

Injections in groups 1, 2, 3 and 4 were performed according to the schedules Q2DX8, i.e. 1 quantity every two days, eight times.

Mice were observed for 2 hours post-injection. Ketamine/Xylazine (80 mg/kg-12 mg/kg; Ref. K-113, Sigma, France) was used to anaesthetize the animals before sacrifice by cervical dislocation. For all animals, the tumor size was measured twice a week with calipers. The tumor volume ($mm^3$) was measured according to the formula: (length×width$^2$)/2.

Statistical Studies
Data Outlined Below were Calculated:
  Tumor growth curves were drawn using the mean tumor volumes (MTV),
  Mean Relative tumor volume (MRTV) was calculated as the ratio between the MTV at time t and the volume at the time of injection (t=D12),
  Tumor growth inhibition (T/C, %) was evaluated as the ratio of the median tumor volumes of treated groups versus vehicle group.

Statistical analyses of tumor volumes (TV), time to reach 'TV', tumor-doubling time (DT), relative tumor volume (RTV) and tumor growth inhibition (T/C) were performed for all groups. Data are expressed as mean±SD. Groups of data were normally distributed. Univariate analysis were performed to assess differences between groups. Statistical significance was then determined using the Student's t test. A $P<0.05$ was considered as statistically significant. The Statistical analysis was performed using XLSTAT (Addinsoft, France).

Body Weight

As shown in table 3, the vehicle had no impact: mouse behavior and body weight gain were normal and no animal died prematurely. No toxicity was observed during the course of the treatment with the test substance 168A-T2 at the dose of 15 mg/kg, a slight body weight gain was observed (+2.45 g).

In contrast, an important toxicity was observed in groups 2, 4 treated with CDDP (−2.70 g and −2.35 g body weight loss respectively). The difference between group 1 versus 2 and 4 and group 3 versus 2 and 4 was statistically significant ($p<0.0001$) but the difference between group 2 and 4 was not statistically significant.

TABLE 2

| Group | Animals n | Treatment | Administration route | Treatment dose (mg/kg/adm) | Administration volume | Treatment schedule |
|---|---|---|---|---|---|---|
| 1 | 5 | Vehicle | IP | 0 | 10 ml/kg | Q2DX8 |
| 2 | 5 | Cisplatin | IP | 5 | | Q2DX8 |
| 3 | 5 | 168A-T2 | IP | 15 | | Q2DX8 |
| 4 | 5 | 168A-T2 & Cisplatin | IP | 15 5 | | Q2DX8 |

TABLE 3

Mean body weight (MBW) of mice bearing CALU-6 tumors treated with the vehicle, CDDP at 5 mg/kg (schedule Q2DX8, G2), 168A-T2 at 10.0 mg/kg (schedule Q2DX8, G3), combined 168A-T2 at 10.0 mg/kg and CDDP at 5 mg/kg (schedule Q2DX8, G4) at D12 and D28.

| Group | Test substance | Treatment dose (mg/kg) | MBW at D12 (g) | MBW at D28 (g) | MBWC D12-D28 (g) |
|---|---|---|---|---|---|
| 1 | Vehicle | 0 | 22.35 ± 1.17 | 24.40 ± 1.19 | +2.36 (±0.59) |
| 2 | Cisplatin | 5.00 | 21.40 ± 0.85 | 18.69 ± 1.97 | −2.70 (±1.57) |
| 3 | 168A-T2 | 15.0 | 21.74 ± 0.89 | 24.20 ± 1.37 | +2.45 (±0.65) |
| 4 | 168A-T2 + Cisplatin | 15.0 + 5.00 | 20.74 ± 1.41 | 18.39 ± 0.74 | −2.35 (±1.99) |

Figure 6:
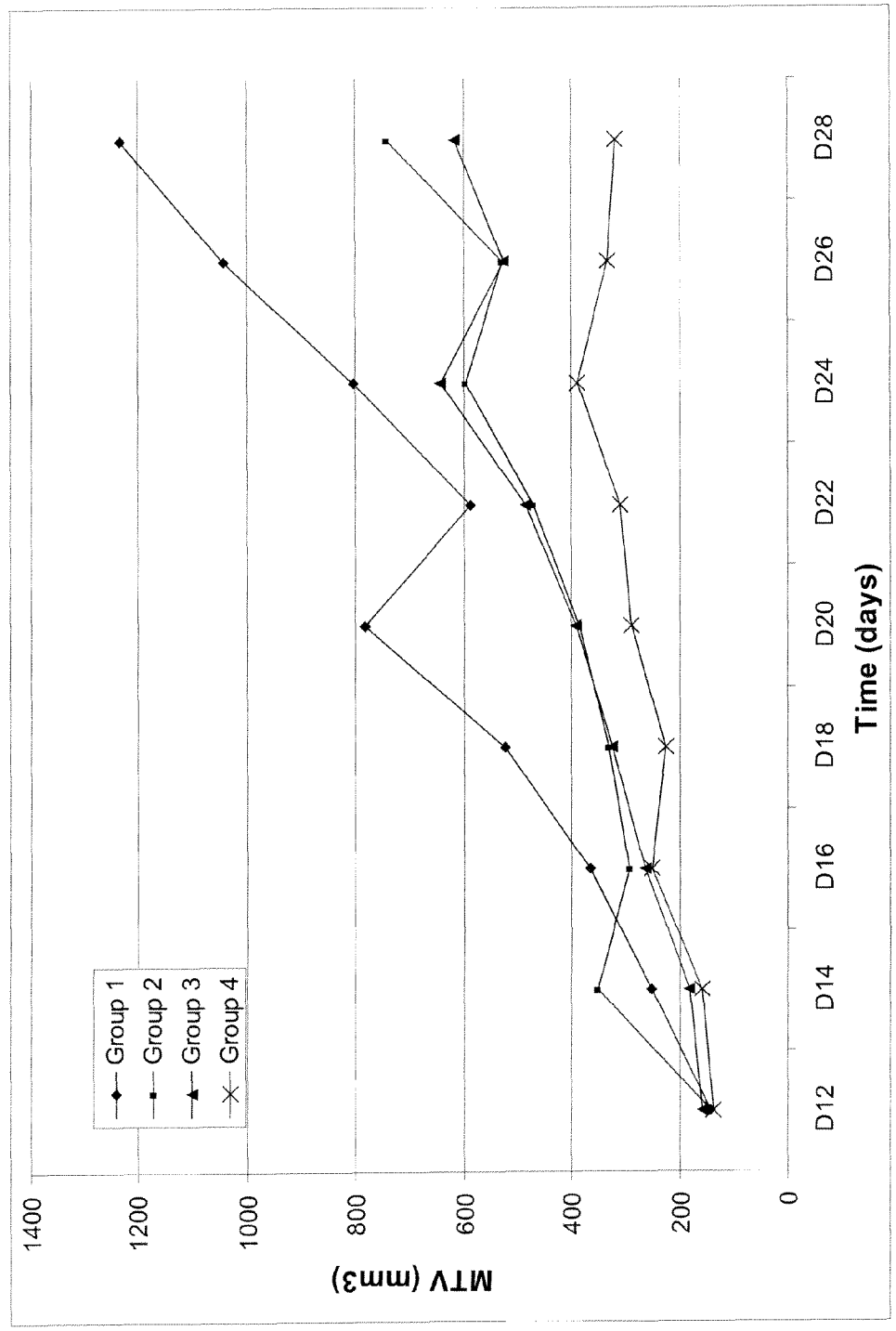
FIG. 6 is a graph representing Mean Tumor Volume (mm$^3$) versus time (days) for different groups of mice treated according to example 8.
Figure 7:
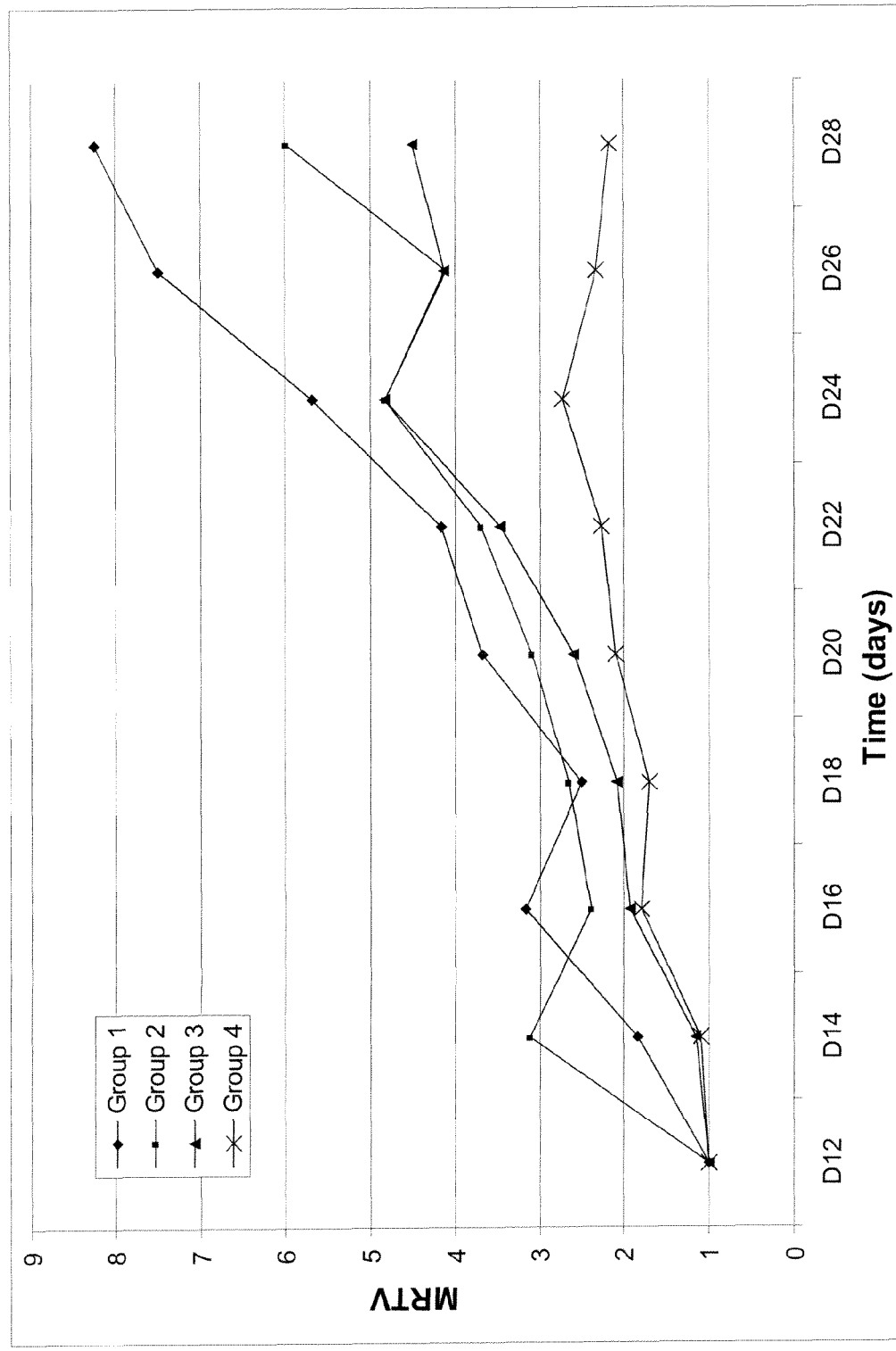
FIG. 7 is a graph representing Mean Relative Tumor Volume (without unit) versus time (days) for different groups of mice treated according to example 8.

The results of mean tumor volume (MTV), mean relative tumor volume (MRTV) and tumor growth parameters (T/C) are shown in FIGS. 6, 7 and in Tables 4, 5 and 6.

The MTV (Table 4, FIG. 6) was decreased at D28 in mice of group 2 treated with CDDP (742.44 mm$^3$) compared to mice of the vehicle group 1 (1233.44 mm$^3$). The MTV at D28 was also decreased in group 3 treated with the test substance 168A-T2 at 15 mg/kg with 1 injection per two days (615.96 mm$^3$). The most important MTV decrease was obtained for animals of group 4 (317.17 mm$^3$). The difference between group 1 and the 2 groups treated with the test substance reach the statistical significativity ($p<0.0001$ vs 4–$p=0.003$ vs 3). The difference between group 2 and 4 was also significant ($p=0.001$). In contrast no statistical difference was observed between group 2 (CDDP alone) and group 3 (168A-T2 alone).

TABLE 4

Mean tumor volume (MTV) of animals bearing CALU-6 cells and treated with vehicle (group 1), CDDP alone (Group 2), 168A-T2 (10.0 mg/kg) (Group 3), or combined with 168A-T2 and CDDP (Group 4) according to the scheduled treatment Q2DX8.

| | MTV (mm$^3$) | | | | | | | | |
|---|---|---|---|---|---|---|---|---|---|
| Group | D12 | D14 | D16 | D18 | D20 | D22 | D24 | D26 | D28 |
| 1 | 142.61 | 252.49 | 365.52 | 522.27 | 784.61 | 588.53 | 803.89 | 1044.02 | 1233.44 |
| 2 | 142.60 | 351.15 | 291.29 | 329.18 | 386.84 | 470.59 | 595.00 | 527.98 | 742.44 |

TABLE 4-continued

Mean tumor volume (MTV) of animals bearing CALU-6 cells and treated with vehicle (group 1), CDDP alone (Group 2), 168A-T2 (10.0 mg/kg) (Group 3), or combined with 168A-T2 and CDDP (Group 4) according to the scheduled treatment Q2DX8.

| | MTV (mm³) | | | | | | | | |
|---|---|---|---|---|---|---|---|---|---|
| Group | D12 | D14 | D16 | D18 | D20 | D22 | D24 | D26 | D28 |
| 3 | 159.22 | 181.94 | 264.20 | 322.99 | 391.90 | 485.42 | 642.24 | 524.95 | 615.96 |
| 4 | 137.68 | 157.35 | 250.14 | 226.39 | 290.70 | 311.24 | 387.85 | 334.10 | 317.17 |

These results were confirmed by the analysis of the MRTV (table 5, FIG. 7). The MRTV for animals of group 1 was 8.24 at D28. For animals of group 2, i.e. treated with CDDP, the MRTV at D28 was 5.98; for animals of group 3, i.e. treated with 168A-T2 (15 mg/kg), the MRTV at D28 was 4.51; eventually, for animals of group 4, i.e. treated with both CDDP and 168A-T2, the MRTV was 2.18.

TABLE 5

Mean Relative tumor volume (MRTV) of animals bearing CALU-6 cells and treated with vehicle (group 1), CDDP alone (Group 2), 168A-T2 (10.0 mg/kg) (Group 3), or combined with 168A-T2 and CDDP (Group 4) according to the scheduled treatment Q2DX8.

| | MRTV | | | | | | | | |
|---|---|---|---|---|---|---|---|---|---|
| Group | D12 | D14 | D16 | D18 | D20 | D22 | D24 | D26 | D28 |
| 1 | 1 | 1.83 | 3.17 | 2.51 | 3.68 | 4.16 | 5.68 | 7.49 | 8.24 |
| 2 | 1 | 3.11 | 2.39 | 2.66 | 3.08 | 3.70 | 4.84 | 4.11 | 5.98 |
| 3 | 1 | 1.15 | 1.93 | 2.08 | 2.60 | 3.47 | 4.83 | 4.14 | 4.51 |
| 4 | 1 | 1.09 | 1.80 | 1.70 | 2.10 | 2.28 | 2.72 | 2.33 | 2.18 |

As shown in table 5 and FIG. 7, MRTV reached 2.18 at D28 for the animals of group 4, which confirmed the synergistic efficacy of 168A-T2 with Cisplatin. Moreover, cisplatin used alone (group 2) or 168A-T2 used alone (group 3) showed close MRTV at D28, suggesting that 168A-T2 is also a potent mono-therapy anti-tumor agent.

TABLE 6

Growth inhibition based on T/C ratio

| | T/C ratio (%) | | | | | | | |
|---|---|---|---|---|---|---|---|---|
| Day | D14 | D16 | D18 | D20 | D22 | D24 | D26 | D28 |
| G2 | −70% | 24% | −6% | 17% | 11% | 15% | 45% | 27% |
| G3 | 37% | 39% | 17% | 29% | 16% | 15% | 45% | 45% |
| G4 | 40% | 43% | 32% | 43% | 45% | 52% | 69% | 74% |

The T/C ratio (table 6), which is a parameter of tumor growth inhibition, revealed a slight anti-tumoral activity of the test substance when used as a monotherapy as it reduced by 27% tumor size compared to the vehicle-treated group 1. However, when combined with CDDP, the inhibition rate reached 74% reduction of tumor size relative to the vehicle-treated group 1.

These results directly demonstrate that 168A-T2 has a potent anti-tumoral activity when it is used alone or in combination with a cytotoxic agent such as CDDP.

The invention claimed is:

1. An isolated polypeptide consisting of:
   SEQ ID NO:4; or
   a fragment of SEQ ID NO: 4 comprising of SEQ ID NO: 12,
   wherein said polypeptide has an anti-angiogenic and an anti-tumour activity.

2. The isolated polypeptide according to claim 1, wherein said isolated polypeptide consists of a fragment of SEQ ID NO: 4 comprising of SEQ ID NO: 12 with at least 20 contiguous amino acids selected from the group consisting of SEQ ID NO: 7, SEQ ID NO: 8, SEQ ID NO: 9, SEQ ID NO: 10, SEQ ID NO: 11 and SEQ ID NO: 12.

3. A pharmaceutical composition comprising:
   one or more pharmaceutically acceptable excipients; and
   at least one isolated polypeptide according to claim 1.

4. A pharmaceutical composition according to claim 3, further comprising at least one another active substance selected from anti-angiogenic substances or anti-tumour substances.

5. A pharmaceutical composition comprising effective amounts of
   an isolated polypeptide according to claim 1, and
   a platinum complex selected from the group consisting of cisplatin and carboplatin.

6. The pharmaceutical composition according to claim 3, being in a form suitable for topical, systemic, oral, subcutaneous, transderm, intramuscular or intra-peritoneal administration.

7. The pharmaceutical composition according to claim 6, wherein said isolated polypeptide is present in an amount from 0.01 to 90% in weight.

8. The pharmaceutical composition according to claim 7, wherein said polypeptide is present in an amount from 0.1% to 10% in weight.

9. The pharmaceutical composition according to claim 8, wherein said polypeptide is present in an amount from 1% to 5% in weight.

* * * * *